US010265891B2

(12) United States Patent
Pletcher

(10) Patent No.: US 10,265,891 B2
(45) Date of Patent: Apr. 23, 2019

(54) ANTIOXIDANT-INFUSED ULTRA HIGH MOLECULAR WEIGHT POLYETHYLENE

(71) Applicant: Zimmer, Inc., Warsaw, IN (US)

(72) Inventor: Dirk Pletcher, Walkerton, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 14/957,790

(22) Filed: Dec. 3, 2015

(65) Prior Publication Data

US 2016/0158976 A1  Jun. 9, 2016

Related U.S. Application Data

(60) Provisional application No. 62/086,936, filed on Dec. 3, 2014.

(51) Int. Cl.
| | | |
|---|---|---|
| *C08J 3/12* | (2006.01) | |
| *B29C 69/02* | (2006.01) | |
| *C08L 23/06* | (2006.01) | |
| *A61L 27/16* | (2006.01) | |
| *A61F 2/30* | (2006.01) | |
| *A61L 27/56* | (2006.01) | |
| *B29C 43/02* | (2006.01) | |
| *B29C 67/00* | (2017.01) | |
| *B29C 70/00* | (2006.01) | |
| *B29C 71/04* | (2006.01) | |
| *B29K 23/00* | (2006.01) | |
| *B29L 31/00* | (2006.01) | |
| *B29K 105/00* | (2006.01) | |

(52) U.S. Cl.
CPC ............... *B29C 43/02* (2013.01); *A61F 2/30* (2013.01); *A61L 27/16* (2013.01); *A61L 27/56* (2013.01); *B29C 67/0029* (2013.01); *B29C 69/02* (2013.01); *B29C 70/00* (2013.01); *B29C 71/04* (2013.01); *C08J 3/128* (2013.01); *A61F 2002/30685* (2013.01); *A61L 2300/428* (2013.01); *B29K 2023/0683* (2013.01); *B29K 2105/0058* (2013.01); *B29K 2995/0088* (2013.01); *B29L 2031/7532* (2013.01)

(58) Field of Classification Search
CPC ..... B29C 43/02; B29C 67/0029; B29C 70/00; B29C 71/04; A61F 2/30; A61F 27/16; A61F 27/56; C08J 3/128
USPC ......................................................... 524/585
See application file for complete search history.

(56) References Cited

U.S. PATENT DOCUMENTS

| | | | |
|---|---|---|---|
| 5,308,549 A | 5/1994 | Laermer et al. |
| 5,414,049 A | 5/1995 | Sun et al. |
| 5,559,167 A | 9/1996 | Mahood |
| 5,577,368 A | 11/1996 | Hamilton et al. |
| 5,721,334 A | 2/1998 | Burstein et al. |
| 5,753,182 A | 5/1998 | Higgins |
| 5,824,411 A | 10/1998 | Shalaby et al. |
| 5,827,904 A | 10/1998 | Hahn |
| 5,879,400 A | 3/1999 | Merrill et al. |
| 6,017,975 A | 1/2000 | Saum et al. |
| 6,087,553 A | 7/2000 | Cohen et al. |
| 6,087,559 A | 7/2000 | Cohen et al. |
| 6,156,845 A | 12/2000 | Saito et al. |
| 6,156,913 A | 12/2000 | Hyatt |
| 6,165,220 A | 12/2000 | McKellop et al. |
| 6,184,265 B1 | 2/2001 | Hamilton et al. |
| 6,204,257 B1 | 3/2001 | Stella et al. |
| 6,228,900 B1 | 5/2001 | Shen et al. |
| 6,231,804 B1 | 5/2001 | Yamauchi et al. |
| 6,242,227 B1 | 6/2001 | Millis et al. |
| 6,242,507 B1 | 6/2001 | Saum et al. |
| 6,245,276 B1 | 6/2001 | McNulty et al. |
| 6,277,390 B1 | 8/2001 | Schaffner |
| 6,391,390 B1 | 5/2002 | Boisseau et al. |
| 6,432,349 B1 | 8/2002 | Pletcher et al. |
| 6,437,048 B1 | 8/2002 | Saito et al. |
| 6,448,315 B1 | 9/2002 | Lidgren et al. |
| 6,464,926 B1 | 10/2002 | Merrill et al. |
| 6,503,439 B1 | 1/2003 | Burstein |
| 6,558,794 B1 | 5/2003 | Fehrenbacher et al. |

(Continued)

FOREIGN PATENT DOCUMENTS

| | | |
|---|---|---|
| AU | 2006350369 A1 | 1/2007 |
| AU | 2006350369 A1 | 8/2008 |

(Continued)

OTHER PUBLICATIONS

US 7,253,214 B2, 08/2007, McKellop et al. (withdrawn)
Bauer, I., et al., "Synthesis of New Organic Phosphites Containing Sterically Hindered Piperidine Groups. Phosphorus, Sulfur, and Silicon and the Related Elements", vol. 28, (1997), 79-103 pgs.

(Continued)

*Primary Examiner* — Kelechi C Egwim

(74) *Attorney, Agent, or Firm* — Schwegman Lundberg & Woessner, P.A.

(57) ABSTRACT

Various embodiments disclosed relate to antioxidant-stabilized materials including ultra high molecular weight polyethylene (UHMWPE), methods of making the same, and medical implants including the same. In various embodiments, the present invention provides a method of adding antioxidant to UHMWPE. The method includes obtaining or providing a porous solid material including UHMWPE. The method includes coating the porous solid material with a liquid composition including at least one antioxidant such that at least some of the liquid composition enters void space of the porous solid material, to provide an antioxidant-infused solid material. The method also includes melt-consolidating the antioxidant-infused solid material, to provide a melt-consolidated material.

18 Claims, 9 Drawing Sheets

(56) References Cited

U.S. PATENT DOCUMENTS

| | | |
|---|---|---|
| 6,562,540 B2 | 5/2003 | Saum et al. |
| 6,620,198 B2 | 9/2003 | Burstein et al. |
| 6,627,141 B2 | 9/2003 | McNulty et al. |
| 6,641,617 B1 | 11/2003 | Merrill et al. |
| 6,664,308 B2 | 12/2003 | Sun et al. |
| 6,664,317 B2 | 12/2003 | King, III |
| 6,692,679 B1 | 2/2004 | McNulty et al. |
| 6,786,933 B2 | 9/2004 | Merrill et al. |
| 6,818,020 B2 | 11/2004 | Sun et al. |
| 6,818,172 B2 | 11/2004 | King et al. |
| 6,852,772 B2 | 2/2005 | Muratoglu et al. |
| 6,853,772 B2 | 2/2005 | Battiato et al. |
| 6,872,764 B2 | 3/2005 | King, III |
| 6,933,026 B2 | 8/2005 | Mauze |
| 7,094,472 B2 | 8/2006 | Du Plessis et al. |
| 7,160,492 B2 | 1/2007 | King |
| 7,166,650 B2 | 1/2007 | Muratoglu et al. |
| 7,214,764 B2 | 5/2007 | King |
| 7,259,198 B2 | 8/2007 | Vaillant |
| 7,304,097 B2 | 12/2007 | Muratoglu et al. |
| 7,323,522 B2 | 1/2008 | Ideno et al. |
| 7,335,697 B2 | 2/2008 | King et al. |
| 7,384,430 B2 | 6/2008 | Greer et al. |
| 7,431,874 B2 * | 10/2008 | Muratoglu ............... A61L 27/16 264/235 |
| 7,435,372 B2 | 10/2008 | Mimmnaugh et al. |
| 7,445,641 B1 | 11/2008 | Ornberg et al. |
| 7,498,365 B2 | 3/2009 | Muratoglu et al. |
| 7,507,774 B2 | 3/2009 | Muratoglu et al. |
| 7,569,620 B2 | 8/2009 | Muratoglu et al. |
| 7,595,074 B2 | 9/2009 | Cholli et al. |
| 7,615,075 B2 | 11/2009 | Kunze et al. |
| 7,635,725 B2 | 12/2009 | Bellare et al. |
| 7,683,133 B2 | 3/2010 | King et al. |
| 7,705,075 B2 | 4/2010 | Kumar et al. |
| 7,705,176 B2 | 4/2010 | Cholli et al. |
| 7,790,095 B2 | 9/2010 | Muratoglu et al. |
| 7,806,064 B2 | 10/2010 | Wellman |
| 7,833,452 B2 | 11/2010 | Muratoglu et al. |
| 7,846,376 B2 | 12/2010 | Abt et al. |
| 7,863,348 B2 | 1/2011 | Abt et al. |
| 8,129,440 B2 | 3/2012 | Rufner et al. |
| 8,178,594 B2 | 5/2012 | Rufner et al. |
| 8,287,784 B2 * | 10/2012 | Dirix ..................... A61L 27/16 264/126 |
| 8,399,535 B2 | 3/2013 | Pletcher |
| 8,470,903 B2 | 6/2013 | Abt et al. |
| 8,664,290 B2 | 3/2014 | Rufner et al. |
| 8,669,299 B2 | 3/2014 | Rufner et al. |
| 8,673,202 B2 | 3/2014 | Abt et al. |
| 9,265,545 B2 | 2/2016 | Rufner et al. |
| 9,277,949 B2 | 3/2016 | Rufner et al. |
| 9,370,602 B2 | 6/2016 | Thomas et al. |
| 9,822,224 B2 | 11/2017 | Rufner et al. |
| 9,926,432 B2 | 3/2018 | Rufner et al. |
| 2001/0027345 A1 | 10/2001 | Merrill et al. |
| 2001/0049401 A1 | 12/2001 | Salovey et al. |
| 2002/0007219 A1 | 1/2002 | Merrill et al. |
| 2002/0156536 A1 | 10/2002 | Harris et al. |
| 2003/0013781 A1 | 1/2003 | Merrill et al. |
| 2003/0045603 A1 | 3/2003 | Salovey et al. |
| 2003/0105182 A1 | 6/2003 | Merrill et al. |
| 2003/0119935 A1 | 6/2003 | Merrill et al. |
| 2003/0127778 A1 | 7/2003 | Scott et al. |
| 2003/0149125 A1 | 8/2003 | Muratoglu et al. |
| 2003/0158287 A1 | 8/2003 | Salovey et al. |
| 2003/0212161 A1 | 11/2003 | McKellop et al. |
| 2004/0051213 A1 | 3/2004 | Muratoglu et al. |
| 2004/0156879 A1 | 8/2004 | Muratoglu et al. |
| 2004/0265165 A1 | 12/2004 | King |
| 2005/0006821 A1 | 1/2005 | Merrill et al. |
| 2005/0019371 A1 | 1/2005 | Anderson et al. |
| 2005/0056971 A1 | 3/2005 | Merrill et al. |
| 2005/0059750 A1 | 3/2005 | Sun et al. |
| 2005/0096749 A1 | 5/2005 | Merrill et al. |
| 2005/0124718 A1 | 6/2005 | Muratoglu et al. |
| 2005/0125074 A1 | 6/2005 | Salovey et al. |
| 2005/0146070 A1 | 7/2005 | Muratoglu et al. |
| 2005/0165495 A1 | 7/2005 | Merrill et al. |
| 2005/0194722 A1 | 9/2005 | Muratoglu et al. |
| 2005/0194723 A1 | 9/2005 | Muratoglu et al. |
| 2005/0267594 A1 | 12/2005 | Merrill et al. |
| 2006/0079597 A1 | 4/2006 | Muratoglu et al. |
| 2006/0115668 A1 | 6/2006 | King et al. |
| 2006/0264541 A1 | 11/2006 | Lederer et al. |
| 2007/0004818 A1 | 1/2007 | Muratoglu et al. |
| 2007/0043137 A1 | 2/2007 | Muratoglu et al. |
| 2007/0059334 A1 | 3/2007 | Abt et al. |
| 2007/0077268 A1 | 4/2007 | King et al. |
| 2007/0114702 A1 | 5/2007 | Muratoglu et al. |
| 2007/0149660 A1 | 6/2007 | Kumar et al. |
| 2007/0191504 A1 | 8/2007 | Muratoglu |
| 2007/0232762 A1 | 10/2007 | Ernsberger et al. |
| 2007/0265369 A1 | 11/2007 | Muratoglu et al. |
| 2007/0267030 A1 | 11/2007 | Muratoglu et al. |
| 2007/0275030 A1 | 11/2007 | Muratoglu et al. |
| 2007/0293647 A1 | 12/2007 | McKellop et al. |
| 2008/0039545 A1 | 2/2008 | Muratoglu et al. |
| 2008/0067724 A1 | 3/2008 | Muratoglu et al. |
| 2008/0090933 A1 | 4/2008 | Muratoglu et al. |
| 2008/0090934 A1 | 4/2008 | Muratoglu et al. |
| 2008/0119582 A1 | 5/2008 | Muratoglu et al. |
| 2008/0133018 A1 | 6/2008 | Salovey et al. |
| 2008/0133021 A1 | 6/2008 | Shen et al. |
| 2008/0139137 A1 | 6/2008 | Guo et al. |
| 2008/0140196 A1 | 6/2008 | Schroeder et al. |
| 2008/0197541 A1 | 8/2008 | Cheal |
| 2008/0214692 A1 | 9/2008 | Muratoglu et al. |
| 2008/0215142 A1 | 9/2008 | Muratoglu et al. |
| 2008/0262120 A1 | 10/2008 | Muratoglu |
| 2008/0274161 A1 | 11/2008 | Muratoglu et al. |
| 2008/0293856 A1 | 11/2008 | Kumar et al. |
| 2008/0318022 A1 | 12/2008 | James et al. |
| 2008/0319137 A1 | 12/2008 | Rufner et al. |
| 2009/0030524 A1 | 1/2009 | Schroeder et al. |
| 2009/0105364 A1 | 4/2009 | Merrill et al. |
| 2009/0118390 A1 | 5/2009 | Abt et al. |
| 2009/0192610 A1 | 7/2009 | Case et al. |
| 2009/0265001 A1 | 10/2009 | Muratoglu et al. |
| 2009/0281624 A1 | 11/2009 | Conteduca et al. |
| 2010/0029858 A1 | 2/2010 | Rufner et al. |
| 2010/0082101 A1 | 4/2010 | Muratoglu et al. |
| 2010/0137481 A1 | 6/2010 | Shen et al. |
| 2010/0190882 A1 | 7/2010 | Muratoglu et al. |
| 2010/0331995 A1 | 12/2010 | Smelt et al. |
| 2011/0028600 A1 | 2/2011 | Rufner et al. |
| 2011/0306698 A1 | 12/2011 | Pletcher |
| 2012/0070600 A1 | 3/2012 | Muratoglu et al. |
| 2012/0157591 A1 | 6/2012 | Rufner et al. |
| 2014/0135415 A1 | 5/2014 | Abt et al. |
| 2014/0194934 A1 | 7/2014 | Rufner et al. |
| 2014/0194935 A1 | 7/2014 | Rufner et al. |
| 2015/0151866 A1 | 6/2015 | Oral |
| 2016/0108184 A1 | 4/2016 | Rufner et al. |
| 2016/0145416 A1 | 5/2016 | Rufner et al. |
| 2016/0280863 A1 | 9/2016 | Pletcher |
| 2017/0335074 A1 | 11/2017 | Abt et al. |
| 2018/0051141 A1 | 2/2018 | Rufner et al. |

FOREIGN PATENT DOCUMENTS

| | | | |
|---|---|---|---|
| AU | 2008236996 A1 | 10/2008 | |
| AU | 2012203503 B2 | 5/2014 | |
| CA | 2619937 A1 | 3/2007 | |
| CA | 2669386 A1 | 8/2008 | |
| CA | 2619502 C | 11/2012 | |
| CS | 221403 B1 | 4/1983 | |
| CZ | 221405 B1 | 2/1986 | |
| EP | 0560279 A1 | 9/1993 | |
| EP | 0727195 A2 | 8/1996 | |
| EP | 0935446 A1 | 8/1999 | |
| EP | 0995449 A1 | 4/2000 | |
| EP | 0560279 B1 | 6/2000 | |
| EP | 0727195 B1 | 8/2002 | |

(56) References Cited

FOREIGN PATENT DOCUMENTS

| | | |
|---|---|---|
| EP | 1421918 A1 | 5/2004 |
| EP | 1647242 B1 | 4/2006 |
| EP | 0935446 B1 | 2/2007 |
| EP | 1421918 B1 | 4/2008 |
| EP | 1647242 B1 | 5/2008 |
| EP | 1924614 A2 | 5/2008 |
| EP | 2046577 A1 | 4/2009 |
| EP | 2083981 A1 | 5/2009 |
| EP | 2150285 A2 | 2/2010 |
| EP | 2395048 A2 | 12/2011 |
| EP | 2150285 B1 | 2/2012 |
| EP | 2578248 A1 | 4/2013 |
| EP | 2277560 B1 | 10/2013 |
| EP | 2395048 B1 | 10/2013 |
| EP | 2172229 B1 | 7/2014 |
| GB | 2288399 A | 10/1995 |
| JP | 11239611 A | 9/1999 |
| JP | 2006515777 A | 6/2006 |
| JP | 2009504283 A | 2/2009 |
| JP | 2009504898 A | 2/2009 |
| JP | 2009504897 A | 5/2009 |
| JP | 2010523805 A | 7/2010 |
| JP | 2012143575 A | 8/2012 |
| JP | 2015097814 A | 5/2015 |
| JP | 5735443 B2 | 6/2015 |
| JP | 5969637 B2 | 7/2016 |
| KR | 20090035724 A | 4/2009 |
| WO | WO-8900755 A1 | 1/1989 |
| WO | WO-9729793 A1 | 8/1997 |
| WO | WO-9801085 A1 | 1/1998 |
| WO | WO-9814223 A1 | 4/1998 |
| WO | WO-0049079 A1 | 8/2000 |
| WO | WO-0105337 A1 | 1/2001 |
| WO | WO-0180778 A1 | 11/2001 |
| WO | WO-03049930 A1 | 6/2003 |
| WO | WO-2004024204 A1 | 3/2004 |
| WO | WO-2004064618 A2 | 8/2004 |
| WO | WO-2004064618 A3 | 8/2004 |
| WO | WO-2004101009 A1 | 11/2004 |
| WO | WO-2005074619 A2 | 8/2005 |
| WO | WO-2006041969 A1 | 4/2006 |
| WO | WO-2007019874 A1 | 2/2007 |
| WO | WO-2007024684 A2 | 3/2007 |
| WO | WO-2007024686 A3 | 3/2007 |
| WO | WO-2007056561 A2 | 5/2007 |
| WO | WO-2007121167 A1 | 10/2007 |
| WO | WO-2008016174 A1 | 2/2008 |
| WO | WO-2008052574 A1 | 5/2008 |
| WO | WO-2008092047 A1 | 7/2008 |
| WO | WO-2008101073 A2 | 8/2008 |
| WO | WO-2008101134 A1 | 8/2008 |
| WO | WO-2008113388 A1 | 9/2008 |
| WO | WO-2008124825 A2 | 10/2008 |
| WO | WO-2008124825 A3 | 10/2008 |
| WO | WO-2009032909 A2 | 3/2009 |
| WO | WO-2009045658 A1 | 4/2009 |
| WO | WO-2009060043 A2 | 5/2009 |
| WO | WO-2009032909 A3 | 12/2009 |
| WO | WO-2010003688 A1 | 1/2010 |
| WO | WO-2010125914 A3 | 11/2010 |
| WO | WO-02010129514 A2 | 11/2010 |
| WO | WO-2010129514 A2 | 11/2010 |
| WO | WO-2012061499 A1 | 5/2012 |
| WO | WO-2013170005 A1 | 11/2013 |
| WO | WO-2015138137 A1 | 9/2015 |
| WO | WO-2016090084 A1 | 6/2016 |
| WO | WO-2016153925 A1 | 9/2016 |
| WO | WO-2016153925 A8 | 9/2016 |

OTHER PUBLICATIONS

John, Ingo, "Evaluation of cross-linked UHMWPE with regards to its suitability as implant material for hip joint shells(Beurteilung von vernetztem UHMWPE hinsichtlich seiner Eignung als Implantatwerstoff für Hüftgelenkschalen)", Technische Universität Berlin, ISBN: 978-3-7983-1934-9 w/ ENglish Translation, (2003), 155 pgs.

U.S. Appl. No. 14/983,006, filed Dec. 29, 2015, Antioxidant Stabilized Crosslinked Ultra-High Molecular Weight Polyethylene for Medical Device Applications.

U.S. Appl. No. 15/073,042, filed Mar. 17, 2016, Melt Stabilized Ultra High Molecular Weight Antioxidant.

"Biomet Orthopedics", Brochure E-POLY HSLPE (EXH20), (2007), 23 pgs.

"E POLY HXLPE Brochure", Biomet Orthopedics, (2007), 23 pgs.

"Japanese Application Serial No. 2008-526378, Response filed Oct. 19, 2012 to Examiners Decision of Final Refusal dated Jun. 19, 2012", (w/ English translation of claims), 13 pgs.

"Japanese Application Serial No. 2010-503206, Examiners Decision of Final Refusal dated May 7, 2013", (w/ English translation), 5 pgs.

"Japanese Application Serial No. 2010-503206, Office Action dated Dec. 4, 2012", (w/ English translation), 7 pgs.

"Japanese Application Serial No. 2010-503206, Response filed Mar. 4, 2013 to Office Action dated Dec. 4, 2012", (w/ English translation), 13 pgs.

"Japanese Application Serial No. 2012-049675, Examiners Decision of Final Refusal dated Sep. 30, 2014", (W/ English Translation), 9 pgs.

"Japanese Application Serial No. 2012-049675, Office Action dated Jan. 30, 2015", (w/ English translation of claims), 16 pgs.

"Japanese Application Serial No. 2012-049675, Office Action dated Sep. 3, 2013", (w/ English translation), 13 pgs.

"Japanese Application Serial No. 2012-049675, Response filed Feb. 28, 2014 to Office Action dated Sep. 3, 2013", (W/ English Translation), 14 pgs.

"Japanese Application Serial No. 2015-016315, Amendment filed Feb. 26, 2015", (W/ English Translation), 8 pgs.

"Joint Replacement Material Developed at the Massachusetts General Hospital", from MA General Hosp. MGH Hotline On-line publication, (Aug. 10, 2007), 1 pg.

"JP 11-239611A, English Translation", 10 pgs.

"New joint replacement material developed at Massachusetts General Hospital and put to first clinic use", news release from Massachusetts General Hospital, accessed May 13, 2008, (Nov. 15, 2010), 2 pgs.

"Opposition Application No. 09013154.1, Opposition Brief filed Apr. 16, 2014", (w/ English Translation), 22 pgs.

"Opposition to EP 2277560, Notice of Opposition filed on Jul. 4, 2014", 14 pgs.

"Opposition to EP 2277560, Response filed Feb. 26, 2015 to Notice of Opposition filed on Jul. 4, 2014", 12 pgs.

"Prevention of Fatigue Cracks in Ultrahigh Morecular Weight Polyethylene Joint Components by the Addition of Vitamin E", J. Biomed. Mater. Res., vol. 48,, (1999), 474-478.

"Studies on the effect of electron beam radiation on the molecular structure of ultra-high molecularweight polyethylene under the influence of a-tocopherol with respect to its application in medical implants", J. Materials Science: Materials in Medicine, vol. 13, No. 10, (2002), 917-921.

"The anti-oxidative properties of a-tocopherol in y-irradiated UHMWPE with respect to fatigue and oxidation resistance", Biomatyerials, vol. 26, (Apr. 1, 2005), 5755-5762.

Badertscher, R. P., et al., "Grafting of a-tocopherol upon y-irradiation UHMWPE probed by model hydrocarbons", Polymer Degradation and Stability, 97, (2012), 2255-2261.

Bauer, I., et al., "Antioxidant interaction between organic phosphites and hindered amine light stabilisers during processing and thermoxidation of polypropylene", Polymer Degradation and Stability, 48(3), (1995), 427-440.

Bauer, I., et al., "Antioxidant interaction between organic phosphites and hindered amine light stabilizers: effects during photoxidation of polypropylene—II", Polymer Degradation and Stability, 55(2), (1997), 217-224.

(56) References Cited

OTHER PUBLICATIONS

Bauer, I., et al., "Hydroperoxide decomposing ability and hydrolytic stability of organic phosphites containing hindered amine moieties (HALS-Phosphites)", Polymer Degradation and Stability. 62(1), (1998), 175-186.
Bragdon, et al., "A New Pin-on-disk wear testing method for simulating wear of polyethylene on cobalt-chrome alloy in total hip arthroplasty", The Journal of Arthoplasty vol. 6, No. 5, (2001), 658-665.
Chmela, S., et al., "HALS-phosphite combinations as light and heat stabilizers for polypropylene", Polymer Degradation and Stability, 39(3), (1993), 367-371.
Davidson, Ernesto, et al., "Characterization of UHMWPE Irradiated with gamma rays stored in E vitamin and thermally treated", Revista De La Facultad De Ingenieria Universidad Central De Venezuela, 26(1),, (2011), 7 pgs.
Greer, K. W., et al., "The Effects of Raw Material, Irradiation Dose, and Irradiation Source on Crosslinking of UHMWPE", Journal of ASTM International, vol. 1, No. 1, (Jan. 2004), pp. 1-11.
Habicher, Wolf D, et al., "Synthesis and antioxidative properties of novel multifunctional stabilizers", Journal of Vinyl and Additive Technology, 7(1), (Mar. 2001), 4-18.
Hahner, U., et al., "Synthesis and antioxidative efficiency of organic phosphites and phosphonites with 2.2.6.6-tetramethylpiperidin-4-yl groups", Polymer Degradation and Stability, 41(2), (1993), 197-203.
Ingo, John, "Evaluation of cross-linked UHMWPE with regards to its suitability as implant material for hip joint shells", Series: Plastics Research published by Manfred H. Wagner, Translation, (2003), 28 pgs.
Kurtz, S, et al., "Trace Concentrations of Vitamin E Protect Radiation Crosslinked UHMWPE from Oxidative Degradation", 53rd Annual Meeting of the Orthopaedic Research Society,.Feb. Paper No. 0020, (Nov. 14, 2007), 1 pg.
Muratoglu, Orhun K., et al., "A Novel Method of Cross-Linking Ultra-High-Molecular-Weight Polyethylene to Improve Wear, Reduce Oxidation, and Retain Mechanical Properties", The Journal of Arthroplasty, vol. 16, No. 2, (2001), 149-160.
Muratoglu, Orhun K, et al., "Larger Diameter Femoral Heads Used in Conjunction With a Highly Cross-Linked Ultra-High Molecular Weight Polyethylene: A New Concept", The Journal of Arthoplasty 16(8) Suppl. 1, (2001), 24-30.
Oral, et al., "Alpha-Tocopherol-doped irradiated UHMWPE for high fatigue resistance and low wear", Biomaterials vol. 25, (2004), 5515-5522.
Oral, et al., "Blending a-Tocopherol with UHMWPE Powder for Oxidation Resistance", Poster 1485, 50th Annual Meeting of Orthopaedic Research Society, San Francisco CA, Mar. 7-10, 2004, Transactions, vol. 29, (2004), 1 pg.
Oral, E, et al., "Characterization of irradiated blends of alpha-tocopherol and UHMWPE", Biomaterials, 26(33), (Nov. 2005), 6657-6663.
Oral, E, et al., "Crosslinked Vitamin E Blended UHMWPE with Improved Grafting and Wear Resistance", ORS Annual Meeting, Poster No. 1181, (2011), 1 pg.
Oral, E, et al., "Trace amounts of grafted vitamin E protect UHMWPE against squalene-initiated oxidation", ORS Annual Meeting, Poster No. 1295, (2011), 1 pg.
Parth, M., et al., "Studies on the effect of electron beam radiation on the molecular structure of ultra-high molecular weight polyethylene under the influence of a-tocopherol with respect to its application in medical implants", Journal of Materials Science: Materials in Medicine, 13(10), (2002), 917-921.
Pletcher, Dirk, et al., "Polymers Compositions Including an Antioxidant", U.S. Appl. No. 12/813,401, filed Jun. 10, 2010, 52 pgs.
Rowell, S, et al., "Detection of Vitamin E in Irradiated UHMWPE by UV-Visible Spectroscopy", ORS 2011 Annual Meeting, Poster No. 1186, (2011), 1 pg.
Rufner, Alicia, et al., "An Antioxidant Stabilized Crosslinked Ultra-High Molecular Weight Polyethylene for Medical Device Applications", U.S. Appl. No. 12/847,741, filed Jul. 30, 2010, 69 pgs.
Shibata, N, et al., "The anti-oxidative properties of alpha-tocopherol in gamma-irradiated UHMWPE with respect to fatigue and oxidation resistance", Biomaterials, 26(29), (Apr. 19, 2005), 5755-5762.
Tomita, N., et al., "Prevention of fatigue cracks in ultrahigh molecular weight polyethylene components by the addition of vitamin E", J Biomed Mater Res., 48(4), (1999), 474-478.
Wannomae, et al., "Vitamin E Stabilized, irradiated UHMWPE for Cruciate Retaining Knee Components", 53rd Annual Meeting of the Orthopaedic Research Society, Poster No. 1783, (Nov. 14, 2007), 1 pg.
Wolf, C, et al., "Radiation Grafting of Vitamin E to Ultra High Molecular Weight Polyethylene", ORS Annual Meeting, Poster No. 1178, (2011), 1 pg.
U.S. Appl. No. 12/100,894, filed Apr. 10, 2008, Antioxidant Stabilized Crosslinked Ultra-High Molecular Weight Polyethylene for Medical Device Applications.
U.S. Appl. No. 12/579,094 U.S. Pat. No. 8,129,440, filed Oct. 14, 2009, Antioxidant Stabilized Crosslinked Ultra-High Molecular Weight Polyethylene for Medical Device Applications.
U.S. Appl. No. 12/967,581 U.S. Pat. No. 8,178,594, filed Dec. 14, 2010, Antioxidant Stabilized Crosslinked Ultra-High Molecular Weight Polyethylene for Medical Device Applications.
U.S. Appl. No. 14/157,708, filed Jan. 17, 2014, Antioxidant Stabilized Crosslinked Ultra-High Molecular Weight Polyethylene for Medical Device Applications.
U.S. Appl. No. 12/813,401 U.S. Pat. No. 8,399,535, filed Jun. 10, 2010, Polymer Compositions Including an Antioxidant.
U.S. Appl. No. 13/403,040 U.S. Pat. No. 8,669,299, filed Feb. 23, 2012, Antioxidant Stabilized Crosslinked Ultra-High Molecular Weight Polyethylene for Medical Device Applications.
U.S. Appl. No. 11/465,743 U.S. Pat. No. 7,846,376, filed Aug. 18, 2006, Ultra-High Molecular Weight Polyethylene Articles and Methods of Forming Ultra High Molecular Weight Polyethylene Articles.
U.S. Appl. No. 12/262,531 U.S. Pat. No. 7,863,348, filed Oct. 31, 2008, Ultra-High Molecular Weight Polyethylene Articles and Methods of Forming Ultra High Molecular Weight Polyethylene Articles.
U.S. Appl. No. 12/942,703 U.S. Pat. No. 8,470,903, filed Nov. 9, 2010, Ultra-High Molecular Weight Polyethylene Articles and Methods of Forming Ultra High Molecular Weight Polyethylene Articles.
U.S. Appl. No. 12/943,160 U.S. Pat. No. 8,673,202, filed Nov. 10, 2010, Ultra-High Molecular Weight Polyethylene Articles and Methods of Forming Ultra High Molecular Weight Polyethylene Articles.
U.S. Appl. No. 14/157,687, filed Jan. 17, 2014, Ultra High Molecular Weight Polyethylene Articles and Methods of Forming Ultra High Molecular Weight Polyethylene Articles.
U.S. Appl. No. 12/847,741, U.S. Pat. No. 8,664,290, filed Jul. 30, 2010, Antioxidant Stabilized Crosslinked Ultra-High Molecular Weight Polyethylene for Medical Device Applications.
U.S. Appl. No. 14/157,695, filed Jan. 17, 2014, Antioxidant Stabilized Crosslinked Ultra-High Molecular Weight Polyethylene for Medical Device Applications.
JPH-11239611A D2 English translation, 7 pgs, (1999).
"Gamma- & Betastrahlen", BGS wiEnglish Translation, [Online]. [Accessed Sep. 27, 2016]. Retrieved from the Internet: <URL: http://de.bgs.eu/wie-funktioniert-es/gamma-betastrahlen/>, 8 pgs.
"Gray (unit)", [Online]. Retrieved from the Internet: <URL: http://en.wikipedia.org/wiki.i/Megagray>, (Accessed Nov. 28, 2013), 5 pgs.
"GUR® (UHMWPE) with vitamin E for orthopedic implants", Ticona—News Release, (Oct. 29, 2007), 2 pgs.
"Radiation crosslinking refines polymers for more efficient use of plastics (Translation of Strahlenvernetzung veredelt Polymere fur den effizienteren Kunststoffeinsatz)", ingenieur.de, [Online]. [Accessed Sep. 29, 2016. Retrieved from the Internet: <URL: https://www.ingenieur.de/technik/facbereiche/verfahrenstechnik/strahlenvernetzung-veredelt-polymere-fuer-effizienteren-kunststoffeinsatz/>, 7 pgs.
Kurtz, Steven, "The UHMWPE Handbook", Ultra-High Molecular Weight Polyethylene in Total Joint Replacement—pp. 22-23, 253, (2004), 5 pgs.

(56) References Cited

OTHER PUBLICATIONS

Labrie, J.P., et al., "AECL Impela Elecfron Beam Industrial Irradiators", Nuclear Instruments and Methods of Physics Research vol. B40/41, (1989), 1153-1157.

* cited by examiner

ANTIOXIDANT-INFUSED ULTRA HIGH MOLECULAR WEIGHT POLYETHYLENE

CLAIM OF PRIORITY

This application claims the benefit of U.S. Provisional Patent Application Ser. No. 62/086,936, filed on Dec. 3, 2014, the benefit of priority of which is claimed hereby, and which is incorporated by reference herein in its entirety.

BACKGROUND OF THE INVENTION

Ultra high molecular weight polyethylene (UHMWPE) is a unique form of polyethylene of extremely high molecular weight, where the molecular weight of commercial grade materials are typically in the range of 2 to 7 million. The molecular weight of commodity polyethylene is typically in the range of 50,000 to 100,000, a factor of 25 or more times lower. UHMWPE is the most widely used material for orthopedic implants that articulate, such as for hip, knee, ankle, elbow and shoulder joint replacement due to osteoarthritis. First implemented in the early 1960's, a major concern for this material has been high wear rate with generation of microscopic wear particles over years of articulation. A known outcome of a high polyethylene particulate burden is a condition known as osteolysis, which results in implant loosening with subsequent need for revision surgery. This concern was addressed in the late 1990's with the introduction of highly crosslinked UHMWPE, which is crosslinked by the use of high energy irradiation such as gamma or electron beam. Crosslinking reduces the wear rate of UHMWPE significantly, but also leaves a high free radical burden in the polyethylene which, if not reduced, can cause oxidation in-vivo, with subsequent reduction in mechanical properties, increasing wear rates, and potential implant failure.

To address the free radical burden, highly crosslinked UHMWPE is most often heat stabilized by raising the material temperature above the melting point of the material. This allows the trapped free radicals that did not participate in crosslinking to promote further crosslinking in the material, or to re-combine, rendering them to an inert state that will not promote premature oxidative degradation. However, the melting process can cause the formation of a significant oxidized layer on the exterior of the material if the melting process is done in an oxygen-containing environment such as air, where sufficient oxygen is present to diffuse into the material in the molten state. This oxidized layer is removed during fabrication of the implant to prevent contamination of the implant with oxidatively-degraded UHMWPE.

SUMMARY OF THE INVENTION

In various embodiments, the present invention provides a method of adding antioxidant to UHMWPE. The method includes obtaining or providing a porous solid material including UHMWPE. The method includes coating the porous solid material with a liquid composition including at least one antioxidant such that at least some of the liquid composition enters void space of the porous solid material, to provide an antioxidant-infused solid material. The method also includes melt-consolidating the antioxidant-infused solid material, to provide a melt-consolidated material.

In various embodiments, the present invention provides a method of adding antioxidant to UHMWPE. The method includes obtaining or providing a porous solid material including UHMWPE. The porous solid material has a void space of about 0.001 vol % to about 80 vol %. The method includes coating the porous solid material with a liquid composition including at least one antioxidant such that at least some of the liquid composition enters the void space of the porous solid material, to provide an antioxidant-infused solid material. The method includes melt-consolidating the antioxidant-infused solid material, to provide a melt-consolidated material. The method includes irradiating the melt-consolidated material using electron beam irradiation, to provide an irradiated material. The method includes heating the irradiated material sufficiently to melt at least part of the irradiated material, to provide a heated material. The method also includes solidifying the heated material, to provide a melt-stabilized material.

In various embodiments, the present invention provides a method of adding antioxidant to UHMWPE. The method includes cold-sintering a UHMWPE powder, to provide a porous solid material including UHMWPE, wherein the porous solid material has a void space of about 0.001 vol % to about 80 vol %. The method includes coating about 90% to about 100% of the porous solid material surface with a liquid composition including at least one antioxidant such that at least some of the liquid composition enters the void space of the porous solid material, to provide an antioxidant-infused solid material. The antioxidant is about 1 wt % to about 100 wt % of the liquid composition. The method includes melt-consolidating the antioxidant-infused solid material, to provide a melt-consolidated material. The method includes irradiating the melt-consolidated material using electron beam irradiation, to provide an irradiated material including UHMWPE having a first concentration of free radicals of at least about $1 \times 10^{15}$ spins/g. The method includes heating the irradiated material sufficient to melt at least part of the irradiated material, to provide a heated material. The method also includes solidifying the heated material, to provide a melt-stabilized material including UHMWPE having a second concentration of free-radicals of less than about $1 \times 10^{15}$ spins/g. The UHMWPE in a surface layer of the melt-stabilized material has an oxidation index that does not exceed about 1.

In various embodiments, the present invention provides a medical implant. The medical implant includes an oxygen-containing-environment-melt-stabilized material including UHMWPE and an antioxidant. The antioxidant is introduced prior to a melt-consolidation step and after a cold-sintering step. The melt-stabilized material is free of post-melt-stabilization-oxidized surface layer removal greater than about 3 mm depth (e.g., less than about 3 mm of the melt-stabilized material is removed). The UHMWPE in a surface layer of the melt-stabilized material has an oxidation index that does not exceed about 1.

Conventional polyethylene and UHMWPE are synthesized in powder form. Conventional polyethylene is processed with shear melting equipment such as an injection molder or an extruder. However, unlike conventional polyethylene, UHMWPE is not easily flowable in the melt state due to the high molecular weight and chain entanglement which act as pseudo-crosslinking and result in resistance to deformation and flow. Processing methods for UHMWPE that involve significant amounts of shear generally degrade the UHMWPE by tearing polymer chains apart, reducing molecular weight and causing a corresponding loss in desirable properties. Therefore, UHMWPE powder is generally processed using heat and pressure under low shear conditions to fuse the boundaries of the powder particles together.

Various embodiments of the present invention provide certain advantages over other melt-stabilized UHMWPE, methods of making the same, and medical implants made from the same. Antioxidants can be added to UHMWPE by mixing with the UHMWPE powder prior to consolidation. However, mixing with the UHMWPE powder prior to consolidation generally leads to a homogeneous distribution of antioxidant within the UHMWPE. Antioxidants can be added to UHMWPE by allowing the antioxidant to diffuse into the UHMWPE before or after melt consolidation. However, controlling the depth of diffusion can be difficult or impossible, and can be limited by at least one of the molecular size of the antioxidant and by the structure and corresponding polarity of the antioxidant. In various embodiments, the depth of infusion of the antioxidant into the UHMWPE material can be independent of (e.g., not limited by) the molecular size or structure and corresponding polarity of the antioxidant. In various embodiments, the infusion depth into a UHMWPE material can be controlled by controlling the concentration of the antioxidant in the liquid composition coated onto the porous solid material, by controlling the quantity of the liquid composition coated onto the porous solid material, or a combination thereof. In various embodiments, the migration depth into the UHMWPE of the antioxidant after infusion (e.g., how far the antioxidant travels in the material past the void space where it begins) can be controlled by controlling at least one of the molecular weight and polarity of the antioxidant in the liquid composition coated onto the porous solid, by controlling the temperature and duration of coating of the liquid composition onto the porous solid material, by controlling the temperature during subsequent melt-consolidation, by controlling the duration of time spent above the melting point during the melt-consolidation, or a combination thereof.

In some embodiments, the method can include forming a UHMWPE material having less or no formation of an oxidized layer on the surface of the UHMWPE. Medical-grade UHMWPE can represent a significant cost in the production of a medical implant including UHMWPE. Oxidation of the surface of UHMWPE during various steps, such as during melt-stabilization (e.g., melting after irradiation), results in the removal and discarding of the oxidized layer due to unsuitability for medical-implant preparation. In some embodiments, as compared to other techniques for preparing UHMWPE materials, the method can form a UHMWPE material that is ready to form into a medical implant with less or no removal of a surface layer. In various embodiments, by avoiding or decreasing removal of an oxidized surface layer of UHMWPE, the method provides cost savings over other methods by decreasing the amount of UHMWPE that is wasted. In some embodiments, the method can avoid formation of a surface oxidation layer even with melt-stabilization in an oxygen-containing atmosphere (e.g., air). In various embodiments, as compared to techniques using an oxygen-free or oxygen-depleted environment for melt-stabilization, the method provides costs savings by avoiding equipment, supplies, and time-consuming techniques needed for generating an oxygen-free or oxygen-depleted environment. In some embodiments, other materials can be infused into the UHMWPE material with the antioxidant during the coating of the liquid composition onto the porous solid material, such as curing agents (e.g., organic peroxides), which can decrease or eliminate a subsequent irradiation crosslinking step.

In some embodiments, the method can include the use of various modifiers for the UHMWPE in the liquid composition, such as crosslinking agents, crosslinking enhancers, surface energy modifiers, antibiotics, and the like. In various embodiments, the method can include controlling the depth or concentration of application of various UHMWPE modifiers or other infused materials by using a molding device, such as a net-shaped molding device; such control can be difficult or impossible using blended materials or using diffusion after melt-consolidation alone.

BRIEF DESCRIPTION OF THE FIGURES

The drawings illustrate generally, by way of example, but not by way of limitation, various embodiments discussed in the present document.

DETAILED DESCRIPTION OF THE INVENTION

Figure 1:
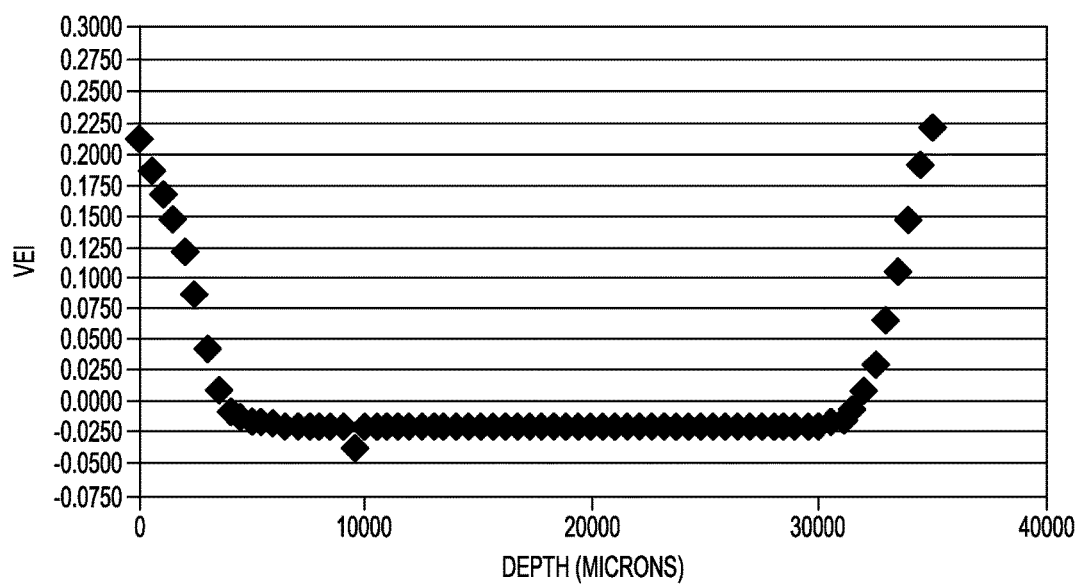
FIG. 1 illustrates the vitamin E index versus depth from the top to the bottom of a melt-consolidated puck, in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R), SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O) CH$_2$C(O)R, C(S)R, C(O)OR, OC(O)R, C(O)N(R)$_2$, OC(O) N(R)$_2$, C(S)N(R)$_2$, (CH$_2$)$_{0-2}$N(R)C(O)R, (CH$_2$)$_{0-2}$N(R) N(R)$_2$, N(R)N(R)C(O)R, N(R)N(R)C(O)OR, N(R)N(R) CON(R)$_2$, N(R)SO$_2$R, N(R)SO$_2$N(R)$_2$, N(R)C(O)OR, N(R) C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 or 12-40 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "heterocyclyl" as used herein refers to aromatic and non-aromatic ring compounds containing 3 or more ring members, of which one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a C$_2$-heterocyclyl can be a 5-ring with two carbon atoms and three heteroatoms, a 6-ring with two carbon atoms and four heteroatoms and so forth. Likewise a C$_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzodioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed herein. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "hydrocarbon" as used herein refers to a functional group or molecule that includes carbon and hydrogen atoms. The term can also refer to a functional group or molecule that normally includes both carbon and hydrogen atoms but wherein all the hydrogen atoms are substituted with other functional groups.

The term "number-average molecular weight" as used herein refers to the ordinary arithmetic mean of the molecular weight of individual molecules in a sample. It is defined as the total weight of all molecules in a sample divided by the total number of molecules in the sample. Experimentally, the number-average molecular weight ($M_n$) is determined by analyzing a sample divided into molecular weight fractions of species i having $n_i$ molecules of molecular weight $M_i$ through the formula $M_n = \Sigma M_i n_i / \Sigma n_i$. The number-average molecular weight can be measured by a variety of well-known methods including gel permeation chromatography, spectroscopic end group analysis, and osmometry. If unspecified, molecular weights of polymers given herein are number-average molecular weights.

The term "weight-average molecular weight" as used herein refers to $M_w$, which is equal to $\Sigma M_i^2 n_i / \Sigma M_i n_i$, where $n_i$ is the number of molecules of molecular weight $M_i$. In various examples, the weight-average molecular weight can be determined using light scattering, small angle neutron scattering, X-ray scattering, and sedimentation velocity.

The term "solvent" as used herein refers to a liquid that can dissolve a solid, liquid, or gas. Nonlimiting examples of solvents are silicones, organic compounds, water, alcohols, ionic liquids, and supercritical fluids.

The term "air" as used herein refers to a mixture of gases with a composition approximately identical to the native composition of gases taken from the atmosphere, generally at ground level. In some examples, air is taken from the ambient surroundings. Air has a composition that includes approximately 78% nitrogen, 21% oxygen, 1% argon, and 0.04% carbon dioxide, as well as small amounts of other gases.

The term "room temperature" as used herein refers to a temperature of about 15° C. to 28° C.

The term "coating" as used herein refers to a continuous or discontinuous layer of material on the coated surface, wherein the layer of material can penetrate the surface and can fill areas such as pores, wherein the layer of material can have any three-dimensional shape, including a flat or curved plane. In one example, a coating can be formed on one or more surfaces, any of which may be porous or nonporous, by immersion in a bath of coating material.

The term "surface" as used herein refers to a boundary or side of an object, wherein the boundary or side can have any perimeter shape and can have any three-dimensional shape, including flat, curved, or angular, wherein the boundary or side can be continuous or discontinuous. While the term "surface" generally refers to the outermost boundary of an object with no implied depth, when the term "pores" is used in reference to a surface, it refers to both the surface opening and the depth to which the pores extend beneath the surface into the substrate.

Method of Adding Antioxidant to UHMWPE.

Oxidation of polyethylene can occur through a free radical pathway, as shown in the following sequence:

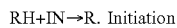
RH+IN→R. Initiation

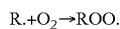
R.+O$_2$→ROO.

ROO.+RH→ROOH+R. Propagation

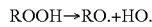
ROOH→RO.+HO.

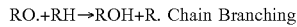
RO.+RH→ROH+R. Chain Branching

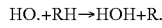
HO.+RH→HOH+R.

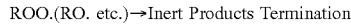
ROO.(RO. etc.)→Inert Products Termination

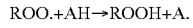
ROO.+AH→ROOH+A.

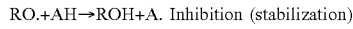
RO.+AH→ROH+A. Inhibition (stabilization)

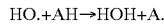
HO.+AH→HOH+A.

wherein
RH=polymer (e.g., polyethylene, UHMWPE)
IN=initiator (e.g., irradiation)
AH=inhibitor (e.g., free-radical scavenging antioxidant)

In various embodiments, the present invention provides a method of adding one or more antioxidants to UHMWPE. The method can include obtaining or providing a porous solid material including UHMWPE. The method can include coating the porous solid material with a liquid composition including at least one antioxidant such that at least some of the liquid composition enters void space of the porous solid material, to provide an antioxidant-infused solid material. The method can include melt-consolidating the antioxidant-infused solid material, to provide a melt-consolidated material.

The method can include cold-sintering a UHMWPE powder to provide the porous solid material. The method can include preheating the melt-consolidated material. The method can include irradiating the melt-consolidated material. The method can include preheating the melt-consolidated material prior to irradiation. The method can include melt-stabilizing the irradiated material.

In certain examples, one or more agents, e.g., bioactive agents, can be added to the material including UHMWPE. Such addition can be accomplished during any stage of preparation but may be desirable after any heat treatments are performed to reduce the likelihood of deactivation of the bioactive agent. Illustrative agents include, but are not limited to, an antibiotic, a steroid, a drug, a growth factor such as bone morphogenic protein, an osteocyte, an osteoclast or other cells, a vitamin, a chondroitin, a glucosamine, a glycosoaminglycan, high energy phosphates such as phosphoenolpyruvate, ATP, 5'-AMP and other small molecule biologics or other chemical or biological agents. In some examples, the material including UHMWPE can be loaded with stem cells, and the material can act as a scaffold to permit growth and differentiation of bone or cartilage within the polymer framework. The presence of an antioxidant in the material including UHMWPE (e.g., via at least one of mixing with the UHMWPE powder and via coating the porous solid material) can act to prevent degradation of the scaffold in its use environment and may also provide some oxidative protection to the bioactive agent or stem cells loaded into the scaffold.

In certain examples, the method of adding antioxidant to UHMWPE can include any suitable physical manipulation before, between, or after any suitable steps of the method (e.g., cold-sintering, coating, melt-consolidating, preheating, irradiating, or melt stabilizing), such as molding, compressing, consolidating, removing material from, or otherwise processing to provide a desired shape, part size, or other physical attributes to render the part suitable for its intended use.

In certain embodiments, additional components may be combined with the material including UHMWPE before, between, or after any suitable steps of the method (e.g., any of cold-sintering, coating, melt-consolidating, preheating, irradiating, and melt-stabilizing). In one embodiment, tribological components such as metal and/or ceramic articulating components and/or preassembled bipolar components may be joined with the material including UHMWPE. In other embodiments, metal backing (e.g., plates or shields) may be added. In further embodiments, surface components such a trabecular metal, fiber metal, Sulmesh™ coating, meshes, cancellous titanium, and/or metal or polymer coatings may be added to or joined with the material including UHMWPE. Radiomarkers or radiopacifiers such as tantalum, steel and/or titanium balls, wires, bolts or pegs may be added. Locking features such as rings, bolts, pegs, snaps and/or cements/adhesives can be added. These additional components may be used to form sandwich implant designs, radiomarked implants, metal-backed implants to prevent direct bone contact, functional growth surfaces, and/or implants with locking features.

Porous Solid Material Including UHMWPE.

The method includes obtaining or providing a porous solid material including UHMWPE. Any suitable proportion of the porous solid material can be the UHMWPE, such as about 1 wt % to about 100 wt % of the porous solid material, about 90 wt % to about 100 wt %, or about 1 wt % or less, or about 2, 3, 4, 5, 10, 15, 20, 25, 30, 35, 40, 45, 50, 55, 60, 65, 70, 75, 80, 85, 90, 95, 96, 97, 98, 99, or about 99.9 wt % or more. The UHMWPE can form a homogeneous or heterogeneous mixture with other components in the porous solid material.

The porous solid material can have any suitable amount of void space therein, wherein the void space is the parts of the porous solid material occupied by porous regions (e.g., not occupied by a solid or liquid). The porous solid material can have about 0.001 vol % to about 80 vol % void space, about 1 vol % to 50 vol % void space, about 1 vol % to about 20 vol % void space, about 5 vol % to about 15 vol % void space, or about 0.001 vol % or less, or about 0.005 vol % void space, 0.01, 0.05, 0.1, 0.5, 1, 2, 3, 4, 5, 6, 7, 8, 9, 10, 12, 14, 16, 18, 20, 25, 30, 35, 40, 45, 50, 55, 60, 65, 70, 75, or about 80 vol % void space or more. The void space in the porous solid material can have any suitable distribution in the porous solid material, such that the method can be performed as described herein. In some embodiments, the void space in the porous solid material can be substantially homogenously distributed.

UHMWPE is a semi crystalline, linear homopolymer of ethylene, which in some embodiments can be produced by stereospecific polymerization with a Ziegler-Natta catalyst at low pressure (6-8 bar) and low temperature (66-80° C.). The synthesis of UHMWPE can result in a fine granular powder. The molecular weight and its distribution can be controlled by process parameters such as temperature, time and pressure. UHMWPE generally has a molecular weight of at least about 2,000,000 g/mol. Suitable UHMWPE materials for use as raw materials may be in the form of a powder or mixture of powders. Examples of suitable UHMWPE materials include GUR® 1020 and GUR® 1050 available from Ticona Engineering Polymers.

In addition to UHMWPE, the porous solid material can include any other suitable component. In certain embodiments, the UHMWPE can be combined with another crosslinkable polymer. The crosslinkable polymer can be any polymer that is crosslinkable using radiation, a chemical crosslinking agent or that can be physically cross-linked under suitable conditions. In some examples, the polymer can be a thermoplastic polymer such as, for example, an acrylonitrile butadiene styrene (ABS) polymer, an acrylic polymer, a celluloid polymer, a cellulose acetate polymer, a cycloolefin copolymer (COC), an ethylene-vinyl acetate (EVA) polymer, an ethylene vinyl alcohol (EVOH) polymer, a fluoroplastic, an ionomer, an acrylic/PVC alloy, a liquid crystal polymer (LCP), a polyacetal polymer (POM or acetal), a polyacrylate polymer, a polyacrylonitrile polymer (PAN or acrylonitrile), a polyamide polymer (PA or nylon), a polyamide-imide polymer (PAI), a polyaryletherketone polymer (PAEK or ketone), a polybutadiene polymer (PBD), a polybutylene polymer (PB), a polybutylene terephthalate polymer (PBT), a polycaprolactone polymer (PCL), a polychlorotrifluoroethylene polymer (PCTFE), a polyethylene terephthalate polymer (PET), a polycyclohexylene dimethylene terephthalate polymer (PCT), a polycarbonate polymer, a polyhydroxyalkanoate polymer (PHA), a polyketone polymer (PK), a polyester polymer, a polyethylene polymer (PE), a polyetheretherketone polymer (PEEK), a polyetherketoneketone polymer (PEKK), a polyetherimide polymer (PEI), a polyethersulfone polymer (PES), a polyethylenechlorinate polymer (PEC), a polyimide polymer (PI), a polylactic acid polymer (PLA), a polymethylpentene polymer (PMP), a polyphenylene oxide polymer (PPO), a polyphenylene sulfide polymer (PPS), a polyphthalamide polymer (PPA), a polypropylene polymer, a polystyrene polymer (PS), a polysulfone polymer (PSU), a polytrimethylene terephthalate polymer (PTT), a polyurethane polymer (PU), a polyvinyl acetate polymer (PVA), a polyvinyl chloride polymer (PVC), a polyvinylidene chloride polymer (PVDC), and a styrene-acrylonitrile polymer (SAN). Illustrative types of polyethylene in addition to the UHMWPE include, for example, ultra low molecular weight polyethylene (ULMWPE), high molecular weight polyethylene (HMWPE), high density polyethylene (HDPE), high density cross-linked polyethylene (HDXLPE), cross-linked polyethylene (PEX or XLPE), medium density polyethylene (MDPE), low density polyethylene (LDPE), linear low density polyethylene (LLDPE) and very low density polyethylene (VLDPE). In some examples, a polypropylene can be used. A polypropylene may be particularly desirable where the final product is a mesh, stent, breast implant material, suture material or other medical device. In one alternative, a polypropylene (or other polymer) may be used as one layer in a multi-layered medical device. Illustrative polypropylenes include, but are not limited to, a homopolymeric polypropylene, a block copolymeric polypropylene, and a random copolymeric polypropylene. In certain examples, the polymers used in the compositions described herein can be copolymerized with one or more monomers or polymers. The porous solid material can be a cold-sintered mixture of UHMWPE and any other suitable component.

In certain examples, the porous solid material can include one or more suitable additives that impart a desired physical or chemical property. Illustrative suitable additives include, but are not limited to, radiopaque materials, antimicrobial materials such as silver ions, antibiotics, and microparticles and/or nanoparticles serving various functions. Preservatives, colorants and other conventional additives may also be used.

In certain embodiments, the porous solid material including UHMWPE can be prepared by a method including blending the UHMWPE powder with other suitable materials, such as a blend with another polymer or a blend with an antioxidant. Such processes include physical mixing, mixing with the aid of a solvent, mixing with the aid of a solvent (e.g., $CO_2$) under supercritical temperature and pressure conditions, and ultrasonic mixing. Suitable mixing processes of these types are also described, for example, in U.S. Pat. Nos. 6,448,315 and 6,277,390, the disclosures of which are hereby incorporated by reference. Cold-sintering can be performed after blending.

The porous solid material can be substantially free of melt-consolidation. The porous solid can be a solid formed prior to a consolidation step that includes melting. For example, the porous solid can be a solid formed from the UHMWPE powder wherein substantially no melting occurs during formation of the porous solid material.

Cold-Sintering.

The porous solid material can be a cold sintered material. The method can include cold-sintering UHMWPE powder, and any optional additional ingredients, to form the porous solid material. The cold-sintering includes application of sufficient pressure under low-shear conditions to fuse the boundaries of the generally spherical powdered UHMWPE particles together. The cold-sintering can include any suitable sub-melting point consolidation technique such as compression molding, direct compression molding, ram extrusion, hot isostatic pressing, ram extrusion, high pressure crystallization, injection molding, and a combination thereof.

The cold-sintering does not melt the UHMWPE. The cold-sintering can generate any suitable maximum temperature in the UHMWPE, such as about 30° C., 35, 40, 45, 50, 55, 60, 65, 70, 75, 80, 85, 90, 95, 100, 105, 110, 115, 120, 125, 130, 135, 140, 145, or about 150° C., so long as substantially no melting of the UHMWPE occurs.

If the cold-sintering is conducted in air, the initial compression of the UHMWPE powder can reduce the air content, and more importantly oxygen content, which can reduce oxidation of UHMWPE during the consolidation and during later parts of the method. In some embodiments, the cold-sintering can be conducted under near inert conditions where the air is displaced by a non-reactive gas such as nitrogen or argon, or under vacuum reduced pressure.

Coating.

The method of adding antioxidant to UHMWPE includes coating the porous solid material with a liquid composition that includes the antioxidant. The porous nature of the porous solid material allows for easy penetration and infusion of a neat antioxidant or an antioxidant solution. The coating can be any suitable coating method that applies the antioxidant in the liquid composition sufficiently such that the antioxidant can penetrate a surface layer of the porous solid material. The coating can be performed using any suitable coating process, such as one or more of brushing, dipping, soaking, immersion with agitation or stirring, spraying, and the like.

The coating can be sufficient for the antioxidant to infuse into a surface layer of the porous solid material that includes any suitable depth from the surface of the porous solid material where the coating is applied, such as about 0 mm to about 1 mm, about 0 mm to about 10 mm deep, about 0 mm to about 20 mm deep, about 1 mm or less, or about 1.5 mm, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, or about 20 mm or more. In various embodiments, the coating can be performed such that the liquid composition does not penetrate past a certain depth of the porous solid material. For example, in some embodiments, the coating penetrates the porous solid material no deeper than about 1 mm or less, or about 1.5 mm, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 mm, or about 20 mm or more. In some embodiments, the coating does not penetrate past the surface layer, wherein the non-surface layer portions of the porous solid material are substantially free of the liquid composition. In various embodiments, the coating penetrates the porous solid material such that in at least one of the melt-consolidated material, the preheated material, the irradiated material, and the melt-annealed material, the antioxidant is present to a depth of about 0 mm to about 1 mm, about 0 mm to about 10 mm deep, about 0 mm to about 20 mm deep, about 1 mm or less, or about 1.5 mm, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, or about 20 mm or more. Subsequent to infusion, in some embodiments the antioxidant can diffuse through the UHMWPE material.

In some embodiments, the antioxidant added via the coating can protect the UHMWPE in the porous solid material from oxidation by oxygen in the air during a subsequent melt-stabilization. For example, the coating can allow the antioxidant in the liquid composition to penetrate into the UHMWPE on the surface of the porous solid material and protect the UHMWPE therein from oxidation by oxygen in the air, as described herein.

The coating can include coating any suitable proportion of the total surface area of the porous solid material. The coating can include selective coating or uniform coating of the porous solid material. The coating can be sufficient to contact at least some of the UHMWPE in the porous solid material and the liquid composition (e.g., the antioxidant in the liquid composition), wherein the UHMWPE can be on the surface or proximate to the surface (e.g., within 1 mm to about 10 mm). In an embodiment wherein the porous solid material only has exposed UHMWPE on a portion of the surface, or only has UHMWPE within about 1-10 mm of only a portion of the surface, the method can optionally include only coating the part of the surface of the porous solid material that includes the UHMWPE or that is proximate to UHMWPE. For example, the coating can include coating about 1% to about 100% of the total surface area of the porous solid material, about 50% to about 100%, about 90% to about 100%, or about 1% or less, or about 2%, 3, 4, 5, 10, 15, 20, 25, 30, 35, 40, 45, 50, 55, 60, 65, 70, 75, 80, 85, 90, 91, 92, 93, 94, 95, 96, 97, 98, 99, 99.5, 99.9, 99.99, or about 99.999% or more.

The coating can be sufficient to provide any suitable weight gain to the porous solid material, such that the antioxidant is suitably applied to the porous solid material. For example, the coating can be sufficient to provide a weight gain of about 0.000,01 g per $cm^2$ surface area of the porous solid material to about 50 g/$cm^2$ surface area, about 0.000,1 g/$cm^2$ surface area to about 1 g/$cm^2$ surface area, about 0.000,01 g/$cm^2$ surface area or less, or about 0.000,1 g/$cm^2$ surface area, 0.000,2, 0.000,5, 0.000,8, 0.001, 0.005, 0.01, 0.05, 0.1, 0.5, 1, 1.5, 2, 2.5, 3, 3.5, 4, 4.5, 5, 6, 7, 8, 9, 10, 12, 14, 16, 18, 20, 25, 30, 35, 40, 45, or about 50 g/$cm^2$ surface area or more.

In some embodiments, the coating can include coating the compression molded cold sintered form by removal of the form from the mold and selectively coating or uniformly coating the de-molded form. Injection under pressure can be used to infuse the antioxidant solution into a compression molded cold sintered form while in the mold with suitable provisions such as an injection port, or into the cold sintered region of a ram extrusion process, where the rate of infusion can be controlled with volumetric rate control and where the amount of pressure utilized will control the depth of penetration.

Diffusion of an antioxidant into consolidated UHMWPE can be limited to antioxidants that are soluble in the UHMWPE, such as vitamin E, which has a long aliphatic chain that is believed to improve solubility. Antioxidant characteristics such as high molecular weight can limit diffusion, while an antioxidant with moderate to high polarity would not be soluble and would not exhibit diffusion into the UHMWPE, even if heated to above the melt temperature for extended periods. In various embodiments, these limitations are addressed by the method of the present invention, infusing antioxidant into the UHMWPE as a porous solid material (e.g., after cold sintering and prior to melt consolidation). Thus, a high molecular weight, water soluble antioxidant (e.g., tannic acid) can be readily infused into a porous solid material including UHMWPE. If solvent is used to dissolve the antioxidant (e.g., a suitable solvent such as water or alcohol), once infused, the solvent vehicle can be removed by heating, with reduced pressure if desired to speed removal of the solvent, leaving the infused antioxidant in position. After infusion and removal of solvent, the antioxidant-infused UHMWPE form can be melt-consolidated by heating above the melt point of the UHMWPE with adequate pressure to fuse the UHMWPE particles together. Further migration into the UHMWPE (e.g., diffusion) may occur for a lower molecular weight antioxidant that is soluble in the UHMWPE, while limited or no migration will occur for a high molecular weight antioxidant or an antioxidant with limited or no solubility in the UHMWPE.

The depth of penetration of the antioxidant into the porous solid material (e.g., depth of infusion) can be controlled by controlling at least one of a pressure of the coating, a duration of the coating, a quantity of the liquid composition used during the coating, a concentration of the antioxidant in the liquid composition used during the coating, a molecular weight of the antioxidant, and a polarity of the antioxidant. Diffusion subsequent to infusion can be controlled by the temperature used during the contacting (e.g., the temperature of the liquid composition, the temperature of the porous solid material, or both), the solubility of the liquid composition in the porous solid material, the molecular size of the antioxidant, the molecular weight of the antioxidant, or a combination thereof.

The coating can include injecting the liquid composition into a mold that includes that porous solid material. In some embodiments, the liquid composition can be injected into the mold under a pressure, wherein the amount of pressure applied (e.g., about 20 psi to 250,000 psi, about 100 psi to about 100,000 psi, about 2,000 to about 10,000 psi, or about 100 psi or less, or about 200 psi, 300, 500, 750, 1,000, 1,500, 2,000, 2,500, 5,000, 7,500, 10,000, 15,000, 20,000, 25,000, 50,000, 75,000, 100,000, 150,000, 200,000, or about 250,000 psi or more) can control the depth of infusion of the liquid composition into the porous solid material. The mold can be part of an apparatus, such as part of a ram extruder, or part of a compression molding device.

Compression molding can include a mold cavity of desired geometry with sufficient volume to hold the powder in non-compressed form. In various embodiments, the powder bulk density can be about half the density of the porous solid material formed from cold-sintering via compression molding. The mold cavity containing the powder can be fitted with a mold ram of the same geometry, where pressure is applied to the ram, which then compresses the powder particles together. The process can include an initial application of high pressure with no heating (e.g., cold-sintering). The initial application of pressure can reduce the bulk density of the non-compressed powder to about 85% to about 95% of the density of the melt-consolidated material. The initial high pressure cold sintering can result in a semi-stable form that can be removed from the mold. The cold sintered form can retain the shape of the mold cavity, and can retain enough integrity that it can be handled. Cold sintering pressures can be any suitable pressure, such as about 20 psi to 250,000 psi, about 100 psi to about 100,000 psi, about 2,000 to about 10,000 psi, or about 100 psi or less, or about 200 psi, 300, 500, 750, 1,000, 1,500, 2,000, 2,500, 5,000, 7,500, 10,000, 15,000, 20,000, 25,000, 50,000, 75,000, 100,000, 150,000, 200,000, or about 250,000 psi or more. Upon removal from the mold, the cold-sintered form can exhibit some level of relaxation or spring-back, where the dimensions exhibit a slight increase after de-molding. The cold-sintered form can be placed back into the cavity with application of low pressure to re-compress the form sufficiently for re-insertion (e.g., after the coating). After the cold-sintering portion of the compression molding process, heat can be applied to melt the UHMWPE compressed material, where the pressure can be reduced once incipient melting has occurred, to prevent extrusion of melted material from any gaps in the mating surfaces of the mold cavity and mold ram. The heating with lower pressure can be maintained until complete fusion between particles has occurred, and any remaining gas in the material between UHMWPE particle voids has been substantially expelled. Once fusion is complete, cooling at a controlled rate can be used, where higher pressure can be applied during the cooling phase to control material shrinkage that can occur due to temperature reduction and crystallization of the molten material.

In some embodiments, a ram extruder can be used for at least one of preparing the porous solid material (e.g., cold-sintering, in a cold-sintering section of the ram extruder) and melt-consolidating the antioxidant-infused solid material (e.g., in a melt-consolidating section of the ram extruder). In some embodiments, the ram extruder can also be used for the coating, such as in a semi-continuous process (e.g., the liquid can be injected into the ram extruder between a cold-sintering section and a melt-consolidating section, optionally with the use of a suitable amount of pressure). Ram extrusion is a semi-continuous process that can be used for melt-consolidation of materials that are difficult or cannot be processed by more typical methods involving shear melting, such as polytetrafluoroethylene and UHMWPE. In some embodiments, the ram extrusion process can include a heavy wall metal cylinder fitted with a feeding port and matching ram to compress the powder below the melting temperature (e.g., cold-sintering section). The ram can also force the compressed cold-sintered plug of UHMWPE powder (e.g., the porous solid material) through the cylinder where the cylinder is fitted with heating to melt the compressed UHMWPE powder as it moves through the cylinder (e.g., melt-consolidation section). A cylinder can be utilized for round shape extrusions. Other shaped die cavities and rams can also be utilized in a similar fashion to form non-cylindrical forms. Ram extrusion can be used for higher volume production with lower labor and equipment costs, and can melt-consolidate at lower cost, such as compared to compression molding.

Liquid Composition Including at Least One Antioxidant.

The method includes coating the porous solid material with a liquid composition that includes one or more antioxidants. In some embodiments, the liquid composition is a neat composition of one or more antioxidants (e.g., one or more antioxidants with no carrier fluid), while in other embodiments the liquid composition is a solution of the one or more antioxidants in one or more suitable solvents (e.g., carrier liquids). The neat antioxidant can be applied if it is a liquid with low enough viscosity, or it can be dissolved in a suitable carrier fluid, such as if it is a viscous liquid or solid. The concentration of the antioxidant can be varied to control the amount of antioxidant infused and distributed in the porous solid material.

The carrier liquid can be any suitable carrier liquid. The carrier liquid can be water (e.g., di-ionized water), or an aqueous solution (e.g., saline). The carrier liquid can be an organic solvent, such as any suitable organic solvent, such as acetone, methanol, ethanol, or propanol (e.g., isopropanol or normal propanol). The carrier liquid, if present, can be any suitable proportion of the liquid including the antioxidant, such as about 1 wt % to about 99 wt %, 5 wt % to about 95 wt %, or about 1 wt % or less, or about 2 wt %, 3, 4, 5, 10, 15, 20, 25, 30, 35, 40, 45, 50, 55, 60, 65, 70, 75, 80, 85, 90, 91, 92, 93, 94, 95, 96, 97, 98, or about 99 wt % or more. In embodiments of the method wherein the liquid composition includes one or more solvents, the method can include heating the material including UHMWPE in subsequent steps sufficiently such that one or more of the one or more solvents is substantially completely evaporated from the material including UHMWPE, for example such that only the one or more antioxidants are left behind. In some embodiments, heating to remove the one or more solvents can occur during the melt-consolidation step, or prior to the melt-consolidating step.

The liquid composition can include any suitable material in addition to the one or more antioxidants and the one or more optional carrier fluids. For example, in some embodiments, the liquid composition includes one or more organic peroxides. In some embodiments, the one or more organic peroxides can provide crosslinking, reducing or eliminating a subsequent irradiation crosslinking step.

Antioxidant.

The antioxidant can be a suitable free-radical scavenger, such that the antioxidant can neutralize a free-radical before the free-radical can react with oxygen to form an oxidized species. The antioxidant can be any suitable antioxidant that allows the method to effectively produce materials including UHMWPE that can resist oxidation, such as melt-stabilized materials including UHMWPE having less or no oxidized layer when melt-stabilized in an oxygen-containing environment. The antioxidant or the multiple antioxidants can be any suitable wt % of the liquid composition, such as about 0.01 wt % to about 100 wt % of the liquid composition, about 1 wt % to about 100 wt %, about 5 wt % to about 100 wt %, about 0.01 wt % or less, or about 0.1 wt %, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, 99.5, 99.9, 99.99, or about 99.999 wt % of the composition or more. The one or more antioxidants can form any suitable wt % of the material including the UHMWPE, such as the antioxidant-infused solid material including UHMWPE, the melt-consolidated material including UHMWPE, the preheated material including UHMWPE, the irradiated material including UHMWPE, or the melt-stabilized material including UHMWPE, such as about 0.01 wt % to about 20 wt %, about 0.1 wt % to about 5 wt %, about 0.01 wt % or less, or about 0.05 wt %, 0.1, 0.2, 0.3, 0.4, 0.5, 0.6, 0.7, 0.8, 0.9, 1, 1.2, 1.4, 1.6, 1.8, 2, 2.2, 2.4, 2.6, 2.8, 3, 3.5, 4, 4.5, 5, 6, 7, 8, 9, 10, 15, or about 20 wt % or more.

In various embodiments, the antioxidant can be at least one of a tocopherol, a tocopherol phosphite (a tocopherol including a phosphite protecting group), a tocotrienol, vitamin E, vitamin E acetate, Irganox® 1010 (pentaerythritol tetrakis(3-(3,5-di-tert-butyl-4-hydroxyphenyl)propionate)), Tinuvin® 622 LD (butanedioic acid dimethyl ester/4-hydroxy-2,2,6,6-tetramethyl-1-piperidine ethanol copolymer), tannic acid, bilberry extract, vitamin C (e.g., ascorbyl palmitate or other lipid soluble forms), a carotene (e.g., vitamin A, licopene), a flavonoid (e.g., flavonol), an isoflavonoid, a neoflavonoid, a lignin (e.g., enterodiol), quinine, ubiquinone (e.g., coenzyme Q10), vitamin K1, a metal (e.g., selenium), glutathione, propyl gallate, octyl gallate, lauryl gallate, resveratrol, rosmarinic acid, rutin, 5-aminosalicylic acid, butylated hydroxy anisole (BHA), butylated hydroxy toluene (BHT), a phenolic compound (e.g., t-butyl hydroquinone), and a monomeric or polymeric hindered amine stabilizer (e.g., derivatives of 2,2,6,6-tetramethylpiperidine, such as 2,2,6,6-tetramethylpiperidin-1-yl)oxidanyl or TEMPO). In some embodiments, the antioxidant can be at least one of vitamin E, vitamin E acetate, vitamin E phosphite (vitamin E including a phosphite protecting group), pentaerythritol tetrakis(3-(3,5-di-tert-butyl-4-hydroxyphenyl)propionate), butanedioic acid dimethyl ester/4-hydroxy-2,2,6,6-tetramethyl-1-piperidine ethanol copolymer, tannic acid, rosemary oil, and bilberry extract. In various embodiments, vitamin E phosphite or a tocopherol phosphite can be used, as described in U.S. Pat. No. 8,399,535, which can be deprotected to provide vitamin E or a tocopherol, respectively, using a suitable deprotection means, such as hydrolysis (e.g., exposure to water with optional acid or base).

For example, the antioxidant can be a compound of the formula (I) or (Ib):

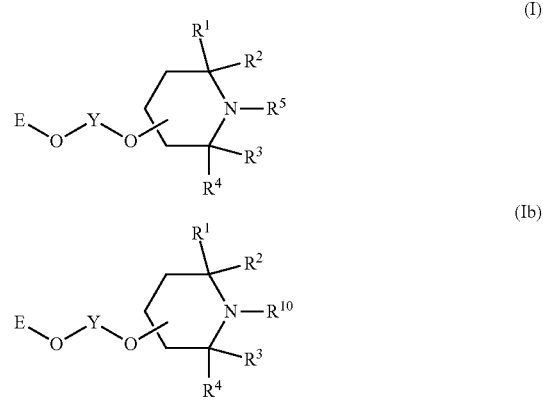

or a salt thereof or combinations thereof. The variables $R^1$, $R^2$, $R^3$, $R^4$, and $R^5$ are each, independently, hydrogen or alkyl. The variable $R^{10}$ is —$OR^{11}$ wherein $R^{11}$ is hydrogen or alkyl, or —O.. The variable E represents a tocopheryl radical or a tocotrienol radical. The variable Y represents:

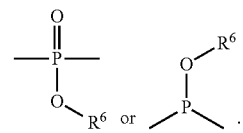

The variable $R^6$ is hydrogen, alkyl, a tocopheryl radical, a tocotrienol radical or a radical of the formula:

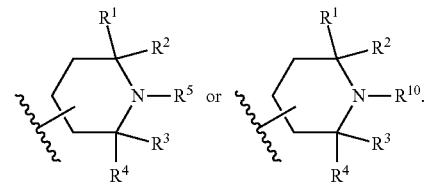

In various embodiments, the method can include deprotecting the antioxidant at any suitable stage of the method (e.g., after an irradiation step). Deprotection can occur via any suitable means, such as via hydrolysis (e.g., exposure to water, as an aqueous solution or in the air).

As used herein, "vitamin E" (e.g., alone or as a derivative such as vitamin E acetate) can refer to at least one of racemic alpha-tocopherol, RRR-alpha-tocopherol, SRR-alpha-tocopherol, SSR-alpha-tocopherol, SRS-alpha-tocopherol, SSS-alpha-tocopherol, RSR-alpha-tocopherol, RRS-alpha-tocopherol, RSS-alpha-tocopherol, racemic beta-tocopherol, RRR-beta-tocopherol, SRR-beta-tocopherol, SSR-beta-tocopherol, SRS-beta-tocopherol, SSS-beta-tocopherol, RSR-beta-tocopherol, RRS-beta-tocopherol, RSS-beta-tocopherol, racemic gamma-tocopherol, RRR-gamma-tocopherol, SRR-gamma-tocopherol, SSR-gamma-tocopherol, SRS-gamma-tocopherol, SSS-gamma-tocopherol, RSR-gamma-tocopherol, RRS-gamma-tocopherol, RSS-gamma-tocopherol, racemic delta-tocopherol, RRR-delta-tocopherol, SRR-delta-tocopherol, SSR-delta-tocopherol, SRS-delta-tocopherol, SSS-delta-tocopherol, RSR-delta-tocopherol, RRS-delta-tocopherol, and RSS-delta-tocopherol.

A tocopherol can have the structure:

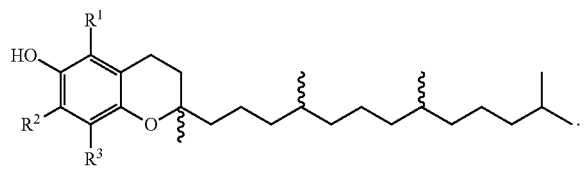

The variables $R^1$, $R^2$, and $R^3$ are each independently selected from hydrogen, substituted or unsubstituted $(C_1-C_{10})$alkyl, and substituted or unsubstituted $(C_1-C_{10})$alkenyl. The stereochemistry of the tocopherol can be racemic or at least one of RRR, SRR, SSR, SRS, RSR, RRS, RSS, and SSS. In some embodiments, $R^1$, $R^2$, and $R^3$ are each $(C_1-C_{10})$alkyl, such as methyl (e.g., alpha-tocopherol). In some embodiments, $R^1$ and $R^3$ are each $(C_1-C_{10})$alkyl, such as methyl, and $R^2$ is hydrogen (beta-tocopherol). In some embodiments, $R^2$ and $R^3$ are each $(C_1-C_{10})$alkyl, such as methyl, and $R^1$ is hydrogen (gamma-tocopherol). In some embodiments, $R^1$ and $R^2$ are each hydrogen and $R^3$ is $(C_1-C_{10})$alkyl, such as methyl (delta-tocopherol).

A tocotrienol can have the structure:

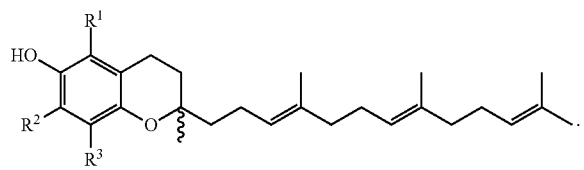

The variables $R^1$, $R^2$, and $R^3$ are each independently selected from hydrogen, substituted or unsubstituted $(C_1-C_{10})$alkyl, and substituted or unsubstituted $(C_1-C_{10})$alkenyl. The stereochemistry of the tocotrienol can be racemic or at least one of R and S. In some embodiments, $R^1$, $R^2$, and $R^3$ are each $(C_1-C_{10})$alkyl, such as methyl (e.g., alpha-tocotrienol). In some embodiments, $R^1$ and $R^3$ are each $(C_1-C_{10})$alkyl, such as methyl, and $R^2$ is hydrogen (beta-tocotrienol). In some embodiments, $R^2$ and $R^3$ are each $(C_1-C_{10})$alkyl, such as methyl, and $R^1$ is hydrogen (gamma-tocotrienol). In some embodiments, $R^1$ and $R^2$ are each hydrogen and $R^3$ is $(C_1-C_{10})$alkyl, such as methyl (delta-tocotrienol). A tocopherol or tocotrienol can be naturally occurring or synthetic.

Melt-Consolidating.

The method includes melt-consolidating the antioxidant-infused solid material. The melt-consolidating can include any suitable melt consolidation procedure. The melt-consolidation can include any suitable above-melting point consolidation technique such as compression molding, direct compression molding, ram extrusion, hot isostatic pressing, ram extrusion, high pressure crystallization, injection molding, and a combination thereof. Melt-consolidating can include any suitable pressure, such as about 20 psi to 250,000 psi, about 100 psi to about 100,000 psi, about 2,000 to about 10,000 psi, or about 100 psi or less, or about 200 psi, 300, 500, 750, 1,000, 1,500, 2,000, 2,500, 5,000, 7,500, 10,000, 15,000, 20,000, 25,000, 50,000, 75,000, 100,000, 150,000, 200,000, or about 250,000 psi or more.

The melt-consolidating generates sufficient heat to melt the UHMWPE. For example, the melt-consolidating can generate a minimum temperature in the UHMWPE of about 60° C., 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 250, 275, or about 300° C. or more, so long as the UHMWPE melts.

The method can include controlling a depth of penetration (e.g., infusion) of the antioxidant in the liquid composition into the porous solid material by controlling at least one of the temperature reached during the melt-consolidating and the duration of the melt-consolidating.

The melt-consolidating can be carried out in air, or can be conducted under near inert conditions where the air is displaced by a non-reactive gas such as nitrogen or argon, or under vacuum reduced pressure.

The melt-consolidated material can have any suitable concentration of antioxidant at various depths from the surface of the material. For example, the coating and melt-consolidating can be sufficient such that the melt-consolidated material has a vitamin E index (VEI, the FTIR ratio of the peak areas between 1275 and 1245 $cm^{-1}$ to the peak areas between 1985 and 1850 $cm^{-1}$) in a surface layer of about −0.1 to about 0.5, about −0.05 to about 0.25, about 0.01 to about 0.25, about 0.05 to about 0.25, about 0.1 to about 0.25, or about −0.1 or less, or about −0.08, −0.06, −0.04, −0.02, −0.01, 0, 0.01, 0.02, 0.04, 0.06, 0.08, 0.1, 0.12, 0.14, 0.16, 0.18, 0.2, 0.22, 0.24, 0.26, 0.28, 0.3, 0.35, 0.4, 0.45, or about 0.5 or more. The surface layer can be a layer of any suitable depth on the material, such as about 0 mm deep (e.g., the top surface most exposed to oxygen), or a layer about 0 mm deep to about 1 mm deep, about 0 mm deep and about 10 mm deep, or about 1 mm deep or less, or about 2 mm, 3, 4, 5, 6, 7, 8, 9, 10, 11, 12, 13, 14, 15, 16, 17, 18, 19, or about 20 mm deep or more. In some embodiments, the VEI can be a gradient that is highest at a depth of 0 mm and that becomes lower at deeper depths. In some embodiments, the VEI can be substantially similar throughout the surface layer or throughout the melt-consolidated material.

The melt-consolidated material can have any suitable concentration of a component of the liquid composition used for the coating at various depths from the surface of the material, such as an antioxidant (e.g., vitamin E), or such as another component. For example, the coating and melt-consolidating can be sufficient such that the melt-consolidated material has a concentration of an antioxidant such as vitamin E in a surface layer of about 0.001 wt % to about 10 wt %, about 0.01 wt % to about 5 wt %, about 0.1 wt % to about 2.5 wt %, about 0.1 wt % to about 1 wt %, or about 0.001 wt % or less, or about 0.01, 0.1, 0.2, 0.4, 0.6, 0.8, 1, 1.2, 1.4, 1.6, 1.8, 2, 2.4, 2.6, 2.8, 3, 3.5, 4, 4.5, 5, 6, 7, 8, 9, or about 10 wt % or more. The surface layer can be a layer of any suitable depth on the material, such as about 0 mm deep (e.g., the top surface most exposed to oxygen), or a layer about 0 mm deep to about 1 mm deep, about 0 mm deep and about 10 mm deep, or about 1 mm deep or less, or about 2 mm, 3, 4, 5, 6, 7, 8, 9, 10, 11, 12, 13, 14, 15, 16, 17, 18, 19, or about 20 mm deep or more. In some embodiments, the concentration of the component can be a gradient that is highest at a depth of 0 mm and that becomes lower at deeper depths. In some embodiments, the concentration of the component can be substantially similar throughout the surface layer or throughout the melt-consolidated material.

Preheating.

In some embodiments, the melt-consolidated material can be preheated prior to an irradiation step, such that when irradiation begins the material being irradiated begins irradiation in a preheated state. In some embodiments, the method includes pre-irradiative preheating. In some embodiments, the method is free of pre-irradiative preheating. In some embodiments, an irradiation step can be performed shortly after melt-consolidation, for example, such that the melt-consolidated material has not yet completely cooled, such that the material is effectively preheated at the time of irradiation.

In some embodiments, the preheating can include heating to a temperature above room temperature and below or above the melting point of the UHMWPE or mixture of UHMWPE and other components, such as about 50° C. to about 110° C., or about 50° C. or less, or about 55° C., 60, 65, 70, 75, 80, 85, 90, 95, 100, 105, 110, 115, 120, 125, 130, 140, 145, or to about 150° C. or more, such that at the time of irradiation onset the material has a preheated temperature. Irradiating.

The method can include irradiating the melt-consolidated material. In some embodiments, the method includes preheating the melt-consolidated material prior to the irradiation. In other embodiments, no preheating occurs prior to irradiation (e.g., the melt-consolidated material is approximately ambient temperature or room temperature when irradiation begins). The irradiating can crosslink the UHMWPE in the melt-consolidated material.

The irradiation can be any suitable irradiation. The irradiation can be visible light radiation, infrared radiation, ultraviolet radiation, electron beam radiation, gamma radiation, or X-ray radiation. Where ionizing radiation is employed to effect the crosslinking reaction, the radiation can be obtained from any suitable source such as an atomic pile, a resonant transformer accelerator, a Van de Graaff electron accelerator, a Linac electron accelerator, a betatron, a synchrotron, a cyclotron, or the like. Radiation from these sources will produce ionizing radiation such as electrons, protons, neutrons, deuterons, gamma rays, X-rays, alpha particles, or beta particles. Where ionizing radiation is used, a sufficient radiation dose rate and/or absorbed dose can be used to induce crosslinking and/or control the degree of crosslinking. In some embodiments, during the irradiation, the temperature of the UHMWPE or mixture of UHMWPE and other components can be maintained below the melting point of the same. In some embodiments, during the irradiation, the temperature of the UHMWPE or mixture of UHMWPE and other components can be allowed to rise above the melting point of the same. In various embodiments, during irradiation, the temperature can be allowed to rise to, or the temperature can be maintained at, about 60° C., 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 250, 275, or about 300° C. or more. In some embodiments, the UHMWPE or mixture of UHMWPE and other components can be preheated prior to irradiation, such as to a temperature above room temperature and below or above the melting point of the UHMWPE or mixture of UHMWPE and other components. In various embodiments, the UHMWPE or mixture of UHMWPE and other components can be preheated to a temperature below the melting point of the same, then subsequently irradiated while maintaining the temperature of the preheated UHMWPE or mixture of UHMWPE and other components below the melting point of the same.

In various embodiments, the irradiating, such as electron-beam irradiation or gamma irradiation, uses a total dose of about 1 kGy to about 100,000 kGy, 10 kGy to about 1000 kGy, about 50 kGy to about 500 kGy, 50 kGy to 300 kGy, or about 1 kGy or less, or about 5, 10, 15, 20, 25, 50, 75, 100, 125, 150, 175, 200, 250, 300, 350, 400, 500, 750, 1,000, 1,250, 1,500, 1,750, 2,000, 2,500, 3,000, 4,000, 5,000, 7,500, 10,000, 15,000, 20,000, 25,000, 50,000, 75,000, or about 100,000 kGy or more. In various embodiments, the irradiating includes using a dose rate of about 0.001 mGy/h to about 500 MGy/h, about 1 mGy/h to about 50 MGy/h, or about 0.001 mGy/h or less, or about 0.005 mGy/h, 0.01, 0.05, 0.1, 0.5, 1, 1.5, 2, 2.5, 3, 3.5, 4, 4.5, 5, 6, 7, 8, 9, 10, 11, 12, 13, 14, 15, 16, 17, 18, 19, 20, 22, 24, 26, 28, 30, 35, 40, 45, 50, 60, 70, 80, 90, 100, 150, 200, 250, 300, 400, or about 500 MGy/h or more.

In certain examples, irradiative crosslinking can be performed in the presence of an additive that can promote or deter crosslinking, depending on the desired level of crosslinking. Illustrative crosslinking promoters include, but are not limited to, trimethylolpropane triacrylate, trimethylolpropane trimethacrylate, pentaerythritol tetraacrylate, and pentaerythritol tetramethacrylate. In certain instances, one or more antioxidants can be present to reduce the degree of crosslinking (e.g., adding before/during cold sintering or added during the coating of the porous solid material with the liquid composition). Alternatively, other reagents that can scavenge free radicals can be present to reduce the degree of crosslinking.

Melt-Stabilizing.

In some embodiments, the method includes heating the melt-consolidated material sufficiently to melt at least part of the melt-consolidated material, to provide a heated material. The heated melt-consolidated material can be an irradiated melt-consolidated material, or a preheated irradiated melt-consolidated material. The method can also include solidifying the heated material, to provide a melt-stabilized material.

The heating can melt any suitable amount of the melt-consolidated material, or of the UHMWPE in the melt-consolidated material, such as about 1 vol % to about 100 vol %, or about 1 vol % or less, or about 2 vol %, 3, 4, 5, 6, 7, 8, 9, 10, 15, 20, 25, 30, 35, 40, 45, 50, 55, 60, 65, 70, 75, 80, 85, 90, 95, 96, 97, 98, or about 99 vol % or more. The heating is sufficient to melt-stabilize the melt-consolidated material, such that at least some of the free radicals in the coated solid material (e.g., free radicals in the UHMWPE, which can be generated during irradiation) can recombine or otherwise be neutralized.

The method can include heating the melt-consolidated material in an environment including oxygen, the heating sufficient to melt at least part of the UHMWPE, to provide a heated material. In some embodiments, the method includes heating the melt-consolidated material in an environment substantially free of oxygen. Various embodiments of the present invention provide a means to reduce the oxidized layer that forms during melt-stabilization of a material including UHMWPE in an oxygen-containing environment such as air. During the melt-stabilization, the antioxidant can scavenge the free radicals present in the outer layer that would normally be oxidized. The heating can occur in an environment including any suitable amount of oxygen. For example, the heating can occur in an environment including ambient air, having about 20-21 vol % oxygen. The heating can occur in an environment having about 1 vol % to about 50 vol % oxygen, about 10 vol % to about 30 vol % oxygen, about 1 vol % oxygen or less, or about 2 vol %, 3, 4, 5, 6, 8, 10, 12, 14, 16, 18, 20, 22, 24, 26, 28, 30, 32, 34, 36, 38, 40, 42, 44, 46, 48, or about 50 vol % oxygen or more.

The heating heats the melt-consolidated material to any suitable temperature, such as about 100° C. to about 400° C., about 140° C. to about 160° C., about 100° C. or less, or about 110° C., 120, 130, 140, 150, 160, 170, 180, 190, 200, 220, 240, 260, 280, 300, 320, 340, 360, 380, or about 400° C. or more. The melt-consolidated material can be heated for any suitable duration, such as about 1 minute to about 7 days, or about 1 hour to about 48 hours, or about 1 minute or less, or about 2 minutes, 3, 4, 5, 10, 15, 20, 25, 30, 35, 40, 45, 50, 55 minutes, 1 hour, 1.5, 2, 2.5, 3, 3.5, 4, 4.5, 5, 6, 7, 8, 9, 10, 11, 12, 13, 14, 15, 16, 17, 18, 19, 20, 21, 22, 23 hours, 1 day, 1.5, 2, 2.5, 3, 3.5, 4, 4.5, 5, 5.5, 6, 6.5 days, or about 7 days or more.

The solidifying can be any suitable solidifying, such that the melted material is allowed to solidify. The solidifying can include allowing the heated material to cool to a temperature below the melting point of the heated material, such as to room temperature. The solidifying can occur in ambient conditions, or the solidifying can occur in a chilled environment. The solidifying can occur in any medium, such as in a gas (e.g., air,) or in a liquid (e.g., water).

The method can be effective to generate a melt-stabilized material including UHMWPE, melt-stabilized in an environment including oxygen, that has decreased or no oxidation in a surface layer of the material, as compared to other methods for melt-stabilization in an oxygen-containing environment. The surface layer including decreased or no oxidation can be a surface layer that corresponds to the entire outer surface of the material, such as for a material including UHMWPE on the entire surface of the material (e.g., the material can be 100% UHMWPE or can have UHMWPE distributed evenly throughout). The surface layer can be a portion of the outer surface that corresponds to a portion of the outer surface of the material, such as for a material including UHMWPE on only a portion of the surface of the material, or such as for a material that was only partially coated with the liquid composition including the antioxidant. The surface layer can be a layer of any suitable depth as measured from the outside of the material, such as about 0 mm to about 1 mm deep, about 0 mm to about 10 mm deep, about 0 mm to about 20 mm deep, about 1 mm or less, or about 1.5 mm, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, or about 20 mm deep or more.

The melt-consolidated material (e.g., the melt-consolidated material, the irradiated melt-consolidated material, or the preheated irradiated melt-consolidated material) can have a first concentration of free-radicals. The first concentration of free-radicals can be any suitable concentration, such as about $1 \times 10^{15}$ spins/gram to about $1 \times 10^{20}$ spins/g, $1 \times 10^{16}$ spins/g to $1 \times 10^{18}$ spins/g, or about $1 \times 10^{15}$ spin/g or less, or about $1 \times 10^{16}$ spins/g, $1 \times 10^{17}$, $1 \times 10^{18}$, $1 \times 10^{19}$, $1 \times 10^{20}$, $1 \times 10^{21}$, $1 \times 10^{22}$, $1 \times 10^{23}$, $1 \times 10^{24}$, $1 \times 10^{25}$, $1 \times 10^{26}$, $1 \times 10^{27}$, $1 \times 10^{28}$, $1 \times 10^{29}$, or about $1 \times 10^{30}$ spins/g or more. The number of spins per gram of the material can be measured in any suitable fashion, such as by electron spin resonance (ESR). The first concentration of free-radicals can be a concentration in the UHMWPE or a concentration in the melt-consolidated material including the UHMWPE. The first concentration of free-radicals can be a concentration in a part or localized area of the material, or can be a concentration throughout the entire material including the UHMWPE. In some embodiments, the first concentration of free-radicals can be generated by and consistent with an amount of irradiation applied to the melt-consolidated material to crosslink the UHMWPE or to crosslink other components in the melt-consolidated material.

The method can include solidifying the heated material, to provide a melt-stabilized material including UHMWPE including a second concentration of free-radicals, wherein the second concentration of free-radicals is less than the first concentration of free-radicals. The melt-stabilization can reduce the concentration of free-radicals. The concentration of free-radicals in the UHMWPE can be reduced. The concentration of free-radicals in other materials can also optionally be reduced, for materials including other materials in addition to UHMWPE, such as other polyethylenes or other polymers. The second concentration of free-radicals in the melt-stabilized material can be any suitable concentration that is lower than the first concentration of free radicals, such as about $1 \times 10^5$ spins/g to about $1 \times 10^{15}$ spins/g, or about $1 \times 10^2$ spins/g or less, or about $1 \times 10^3$ spins/g, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$ spins/g, $1 \times 10^{15}$ spins/g or more. The number of spins per gram of the material can be measured in any suitable fashion, such as by electron spin resonance (ESR). The second concentration of free-radicals can be a concentration in the UHMWPE or a concentration in all the materials the melt-stabilized material including the UHMWPE, corresponding to the part or localized area where the first concentration of free-radicals is determined. The second concentration of free-radicals can be a concentration in a part or localized area of the material (e.g., corresponding to a part or localized area where the first concentration of free-radicals is measured), or can be a concentration throughout the melt-stabilized material including the UHMWPE. The second concentration of free-radicals can be any suitable proportion of the first concentration of free-radicals. For example, the second concentration of free-radicals can be about 1% to about 0.000,1% of the first concentration of free-radicals, about 0.1% to about 0.001%, or about 1% or more, or about 0.5%, 0.1, 0.05, 0.01, 0.005, 0.001, 0.000,5, or about 0.000,1% or less.

As used herein, "oxidation index" refers to an area ratio of fourier transform infrared (FTIR) peaks at 1765-1680 cm$^{-1}$ (e.g. carbonyl peaks) to FTIR peaks 1392-1330 cm$^{-1}$ (e.g., methyl peaks), wherein the area of the carbonyl absorptions centered near 1720 cm$^{-1}$ is related to the amount of chemically bound oxygen present in the material, and the intensity (area) of the C—H absorption centered near 1370 cm$^{-1}$ is used to normalize for the sample's thickness. A surface layer (e.g., the entire surface, or only part of the surface, of any suitable depth) of the melt-stabilized material can have an oxidation index that does not exceed 1 (e.g., the average oxidation index of the surface layer does not exceed an oxidation index of 1 or any portion of the surface layer does not exceed an oxidation index of 1). For example, in some embodiments, the surface layer of the melt-stabilized material has an oxidation index that does not exceed 0.5, or that is about 0.001 to about 1, 0.01 to about 0.5, or about 0.001 or less, or that is equal to or less than about 0.002, 0.003, 0.004, 0.005, 0.006, 0.008, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, 0.5, 0.6, 0.7, 0.8, 0.9, or about 1 or more. The surface layer can be a layer of any suitable depth on the material, such as about 0 mm deep (e.g., the top surface most exposed to oxygen), or a layer about 0 mm deep to about 1 mm deep, about 0 mm deep and about 10 mm deep, or about 1 mm deep or less, or about 2 mm, 3, 4, 5, 6, 7, 8, 9, 10, 11, 12, 13, 14, 15, 16, 17, 18, 19, or about 20 mm deep or more.

The melt-stabilized material can have any suitable concentration of antioxidant at various depths from the surface of the material. For example, the coating, melt-consolidating, and melt-stabilization (optionally including irradiating and preheating) can be sufficient such that the melt-stabilized material has a vitamin E index (VEI, the FTIR ratio of the peak areas between 1275 and 1245 cm$^{-1}$ to the peak areas between 1985 and 1850 cm$^{-1}$) in a surface layer of about −0.1 to about 0.5, about −0.05 to about 0.25, about 0.01 to about 0.25, about 0.05 to about 0.25, about 0.1 to about 0.25, or about −0.1 or less, or about −0.08, −0.06, −0.04, −0.02, −0.01, 0, 0.01, 0.02, 0.04, 0.06, 0.08, 0.1, 0.12, 0.14, 0.16, 0.18, 0.2, 0.22, 0.24, 0.26, 0.28, 0.3, 0.35, 0.4, 0.45, or about 0.5 or more. The surface layer can be a layer of any suitable depth on the material, such as about 0 mm deep (e.g., the top surface most exposed to oxygen), or a layer about 0 mm deep to about 1 mm deep, about 0 mm deep to about 10 mm deep, or about 0.01 mm deep to about 20 mm deep, or about 1 mm deep or less, or about 2 mm, 3, 4, 5, 6, 7, 8, 9, 10, 11, 12, 13, 14, 15, 16, 17, 18, 19, or about 20 mm deep or more. In some embodiments, the VEI can be a gradient that is highest at a depth of 0 mm and that becomes lower at deeper depths. In some embodiments, the VEI can be substantially similar throughout the surface layer or throughout the melt-stabilized material.

The melt-stabilized material can have any suitable concentration of a component of the liquid composition used for the coating at various depths from the surface of the material, such as an antioxidant (e.g., vitamin E), or such as another component. For example, the coating, melt-consolidating, and melt-stabilization (optionally including irradiating and preheating) can be sufficient such that the melt-stabilized material has a concentration of an antioxidant such as vitamin E in a surface layer of about 0.001 wt % to about 10 wt %, about 0.01 wt % to about 5 wt %, about 0.1 wt % to about 2.5 wt %, about 0.1 wt % to about 1 wt %, or about 0.001 wt % or less, or about 0.01, 0.1, 0.2, 0.4, 0.6, 0.8, 1, 1.2, 1.4, 1.6, 1.8, 2, 2.4, 2.6, 2.8, 3, 3.5, 4, 4.5, 5, 6, 7, 8, 9, or about 10 wt % or more. The surface layer can be a layer of any suitable depth on the material, such as about 0 mm deep (e.g., the top surface most exposed to oxygen), or a layer about 0 mm deep to about 1 mm deep, about 0 mm deep and about 10 mm deep, or about 1 mm deep or less, or about 2 mm, 3, 4, 5, 6, 7, 8, 9, 10, 11, 12, 13, 14, 15, 16, 17, 18, 19, or about 20 mm deep or more. In some embodiments, the concentration of the component can be a gradient that is highest at a depth of 0 mm and that becomes lower at deeper depths. In some embodiments, the concentration of the component can be substantially similar throughout the surface layer or throughout the melt-stabilized material.

UHMWPE Material and Medical Implant Including the Same.

In various embodiments, the present invention provides a material including UHMWPE and an antioxidant. The material including UHMWPE can be any material including UHMWPE produced by an embodiment of the method described herein. For example, the material including UHMWPE can be the antioxidant-infused solid material including UHMWPE, the melt-consolidated material including UHMWPE, the preheated material including UHMWPE, the irradiated material including UHMWPE, or the melt-stabilized material including UHMWPE. The material including UHMWPE can be at least one of the melt-consolidated antioxidant-infused solid material, the irradiated melt-consolidated antioxidant-infused solid material, the irradiated preheated melt-consolidated antioxidant-infused solid material, the irradiated and melt-stabilized melt-consolidated antioxidant-infused solid material, and the irradiated preheated and melt-stabilized antioxidant-infused solid material.

In various embodiments, the present invention provides a melt-stabilized material made by any suitable embodiment of a method described herein. For example, in various embodiments, the present invention provides an oxygen-containing-environment-melt-stabilized material including UHMWPE and an antioxidant, the antioxidant introduced prior to a melt-consolidation step and after a cold-sintering step, the melt-stabilized material being free of post-melt-stabilization oxidized surface layer removal greater than about 1 mm depth, 1.5, 2, 2.5, 3, 3.5, 4, 4.5, 5, 5.5, or greater than about 6 mm depth, wherein the UHMWPE in a surface layer of the melt-stabilized material has an oxidation index that does not exceed 1.

In various embodiments, the present invention provides a medical implant including any suitable material including UHMWPE that can be produced by an embodiment of the method described herein. The method of adding antioxidant to UHMWPE can include generating a medical implant from the resulting material, such that the method is a method of making a medical implant. In some embodiments, various amounts of the surface of the melt-stabilized material can be removed during processing and machining the material into the desired shape for the implant, such as about 0 mm to about 1 mm, about 0 mm to about 5 mm, about 0 mm to about 10 mm, about 0.1 mm or less, or about 0.5 mm, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, or about 20 mm or more. In some embodiments, the medical implant can be an orthopedic implant. In various embodiments, the medical implant can form or be part of an artificial hip, hip liner, knee, knee liner, disk replacement, shoulder, elbow, foot, ankle, finger, mandible, or bearings in an artificial heart.

EXAMPLES

Various embodiments of the present invention can be better understood by reference to the following Examples which are offered by way of illustration. The present invention is not limited to the Examples given herein.

The vitamin E/HALS phosphite adduct used in Example 2 was synthesized as follows. Dichloromethane ($CH_2Cl_2$) and triethylamine (TEA) were dried with type 3A, 8-12 mesh activated molecular sieves. Vitamin E ($2.292 \times 10^{-2}$ mole, 9.8732 g, all racemic d,l-α-tocopherol, VE) was added to a clean, dry three neck Schlenk-style reaction flask with magnetic stir bar and dry $N_2$ purge inlet. 1,2,2,6,6-Pentamethyl-4-piperidinol ($4.585 \times 10^{-2}$ mole, 7.8529 g) was added into reaction flask. Dry $CH_2Cl_2$ solvent (15 mL) was added to the reaction flask mixture. Stirring was commenced with under dry $N_2$ purge until solids were dissolved. Dry TEA (10 mL, approximately $3.5 \times 10^{-2}$ mole) was added and mixed under dry $N_2$ purge. Quantitatively, $2.292 \times 10^{-2}$ mole of $PCl_3$ (2.00 ml) was added to 10 ml dry $CH_2Cl_2$ solvent and dissolved. Dry $N_2$ purge was maintained while adding dropwise to the VE-TEA mixture with stirring. Three 5 ml aliquots of dry $CH_2Cl_2$ solvent were used to quantitatively wash in the diluted $PCl_3$ mixture remaining in the emptied delivery flask. After one hour, the temperature of reaction mixture was slowly raised to 40° C. with dry $N_2$ purge and reflux condenser attached. The temperature was maintained at 40° C. for one hour. The reaction mixture was cooled to ambient temperature. Precipitate was filtered off under dry $N_2$ purge using a Schlenk course glass frit treated with Dicalite speed plus filtering aid. A condenser with collection flask was added, and the reaction mixture was slowly heated to 95° C. under dry $N_2$ purge, which was maintained until all volatiles were distilled off. The reaction mixture was cooled to ambient temperature. Dry $CH_2Cl_2$ solvent (15 mL) was added. Precipitate was filtered off under dry $N_2$ purge using Schlenk course glass frit treated with Dicalite speed plus filtering aid.

The vitamin E/HALS phosphite adduct used in Example 4 was synthesized as follows. Dichloromethane ($CH_2Cl_2$) and triethylamine (TEA) were dried with type 3A, 8-12 mesh activated molecular sieves. Vitamin E ($3.439 \times 10^{-2}$ mole, 14.8121 g, all racemic d,l-α-tocopherol, VE) was added to a clean, dry three neck Schlenk style reaction flask with magnetic stir bar and dry $N_2$ purge inlet. 1,2,2,6,6-Pentamethyl-4-piperidinol ($1.720 \times 10^{-2}$ mole, 2.9453 g) was added into reaction flask. Dry $CH_2Cl_2$ solvent (15 mL) was added to the reaction flask mixture. Stirring was commenced under dry $N_2$ purge, until solids were dissolved. Dry TEA (7.5 mL, approximately $3.5 \times 10^{-2}$ mole) and mixed under dry $N_2$ purge. Quantitatively, $PCl_3$ ($1.720 \times 10^{-2}$ mole, 1.50 ml) was added to 10 mL dry $CH_2Cl_2$ solvent and dissolved. The $PCl_3$ solution was maintained under dry $N_2$ purge while adding drop-wise to the VE-TEA mixture with stirring. Three 5 mL aliquots of dry $CH_2Cl_2$ solvent were used to quantitatively wash in the diluted $PCl_3$ mixture remaining in the emptied delivery flask. After one hour, the temperature of reaction mixture was slowly raised to 40° C. with dry $N_2$ purge and reflux condenser attached. The temperature was maintained at 40° C. for one hour. The reaction mixture was cooled to ambient temperature. Precipitate was filtered off under dry $N_2$ purge using Schlenk course glass frit treated with Dicalite speed plus filtering aid. A condenser with collection flask was added, and the reaction mixture was slowly heated to 95° C. under dry $N_2$ purge, which was maintained until all volatiles were distilled off. The reaction mixture was cooled to ambient temperature. Dry $CH_2Cl_2$ solvent (15 mL) was added. Precipitate was filtered off under dry $N_2$ purge using Schlenk course glass frit treated with Dicalite speed plus filtering aid.

Example 1. Vitamin E

Ticona GUR 1020 UHMWPE powder was cold sintered in a 2 inch diameter cylindrical compression under 21 tons of force (42,000 lbs) for 30 minutes at ambient temperature. The cold sintered puck weight was about 112 grams. A 17 wt % solution of vitamin E dissolved in isopropyl alcohol was applied uniformly to the exterior of the cold sintered cylindrical form with a cotton swab. The total vitamin E applied was approximately four to five grams. The cold sintered form readily absorbed the entire solution applied. The form was allowed to dry for 12 hours at ambient temperature, under nitrogen purge. The form was then inserted back into the compression mold, and was consolidated under pressure above the melting point of the UHMWPE. After full consolidation by compression molding, the puck was sectioned and microtome films were obtained at the center from top to bottom, and from side to side, both FTIR scans intersecting the geometric center of the form.

Figure 2:
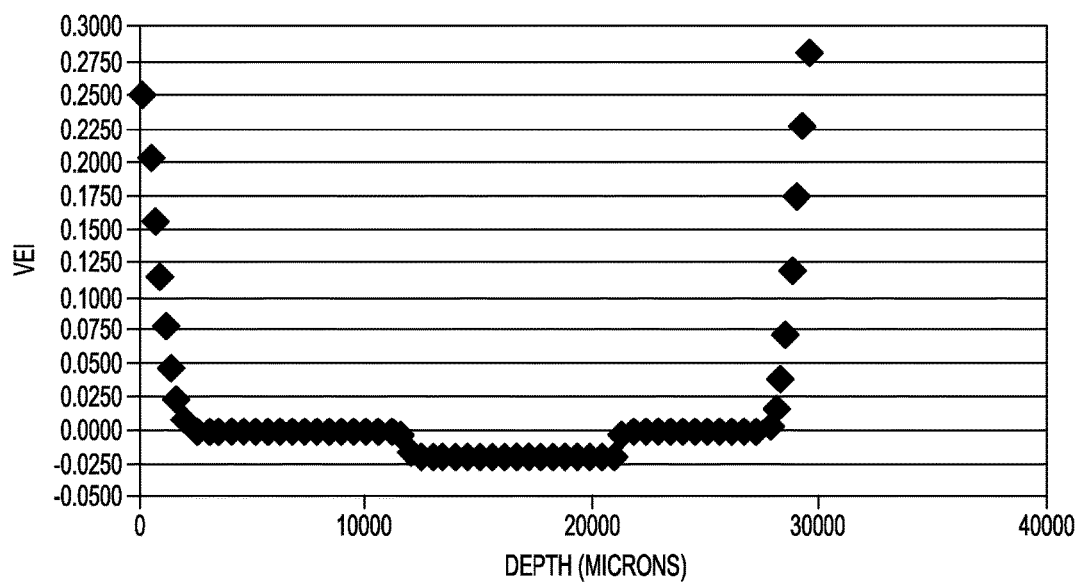
FIG. 2 illustrates the vitamin E index versus depth from one side to the other side of a melt-consolidated puck, in accordance with various embodiments.

Films microtomed from each material/condition were evaluated for vitamin E content, reported as vitamin E index (VEI), which is the FTIR ratio of the peak areas between 1275 and 1245 $cm^{-1}$ to the peak areas between 1985 and 1850 $cm^{-1}$. Results are shown in FIGS. 1-2. FIG. 1 illustrates the VEI versus depth from the top to the bottom of the puck. FIG. 2 illustrates the VEI versus depth from one side to the other side of the puck.

Example 2. Vitamin E/Hindered Amine Light Stabilizer (HALS) Phosphite Adduct The procedure of Example 1 was followed, using a 2.5 inch diameter mold using as the antioxidant a phosphite adduct of one molecule of vitamin E and two molecules of the hindered amine light stabilizer 1,2,2,6,6-pentamethyl-4-piperidinol (e.g., wherein the alcohol group of each of these three molecules has a bond to a phosphorus atom in place of the H of the alcohol).

Dark lines were present in a film taken from the top-right portion of the puck, which appeared to be dark material between unconsolidated flakes of UHMWPE. FTIR detected that the antioxidant penetrated at a depth of 7 mm from the top surface of the puck, 5.8 mm from the left surface, 6.2 mm from the right surface and 4.8 mm from the bottom, with an average depth of penetration of 6 mm. An FTIR spectrum of one of the dark lines appeared to indicate the HALS-vitamin E phosphite adduct, the HALS, vitamin E, and moisture.

Example 3. Chemassorb® 944, Butylated Hydroxy Toluene (BHT), Tannic Acid

The procedure of Example 1 was followed, using a 2.5 inch diameter mold using as the antioxidant Chemassorb® 944 (oligomeric HALS dissolved in hexane with 2.5 wt % solids), butylated hydroxy toluene (BHT dissolved in hexane with 2.5 wt % solids), and tannic acid (dissolved in acetate at 2.5 wt %).

For the Chemassorb® 944, lines of antioxidant were evident in films from the top and bottom of the puck, and lines were evident in films from the left and right of the puck. Multiple layers of the antioxidant were evident throughout the sample. FTIR detected the antioxidant penetrated to a depth of 5.5 mm from the top surface of the puck, 6.5 mm from the left surface, 6.0 mm from the right surface and 6.5 mm from the bottom, with an average depth of penetration of 6.1 mm.

For the BHT, faint lines of antioxidant were seen in films from the top and bottom of the puck, but no lines were evident in films from the left and right of the puck. FTIR detected the antioxidant throughout most of the cross section of the puck, showing the antioxidant penetrated to a depth of 7.0 mm from the top surface of the puck, 8.0 mm from the left surface, 8.0 mm from the right surface and 7.0 mm from the bottom, with an average depth of penetration of 7.5 mm.

For the tannic acid, lines of antioxidant were evident in the films from the top and bottom of the puck, and in the films from the left and right of the puck. FTIR detected the antioxidant penetrated to a depth of 10.0 mm from the top surface of the puck, 10.0 mm from the left surface, 12.0 mm from the right surface and 9.5 mm from the bottom, with an average depth of penetration of 10.4 mm. Low levels of antioxidant were detected throughout the puck from left to right.

Example 4. Oxidation Testing

The procedure of Example 1 was followed four times, using a 2.5 inch diameter mold, using four different conditions: (4-1) no antioxidant treatment, (4-2) using 5 wt % vitamin E solution in isopropanol, (4-3) using 5 wt % vitamin E phosphite in hexane (3 moles vitamin E reacted with 1 mole $PCl_3$, as per U.S. Pat. No. 8,399,535), and (4-4) using 5 wt % vitamin E/HALS phosphite adduct in hexane. The vitamin E/HALS phosphite adduct was a phosphite adduct of two molecules of vitamin E and one molecule of the hindered amine light stabilizer 1,2,2,6,6-pentamethyl-4-piperidinol (e.g., wherein the alcohol group of each of these three molecules has a bond to a phosphorus atom in place of the H of the alcohol). The samples were irradiated with 100 kGy e-beam irradiation and melt annealed in air for 14 h at 150° C., to form Samples 4-1, 4-2, 4-3, and 4-4.

Oxidation levels were determined through the blocks at center from top to bottom and side to side of each block, bottom denoting the surface the block was setting on during the melt stabilization process. The FTIR Oxidation Index (OI) was determined per ASTM F2102-06. Following the ASTM F2102-06 protocol, 100-200 micron thick films were microtomed from the block of material, with the top indicative of the initial incident irradiation face. The film was scanned with an FTIR spectrophotometer using an indexing microscopic attachment to obtain infrared spectra at 200 micron intervals across the entire length of the film. The oxidation index at various locations scanned was then calculated using the ratio of the oxidation peak (1765-1680 $cm^{-1}$, centered at 1720 $cm^{-1}$) to a control peak that does not change with irradiation (1392-1330 $cm^{-1}$, centered at 1370 $cm^{-1}$).

The trans-vinylene index (TVI) throughout the Examples is determined as the area of the infrared absorption peak centered near 965 $cm^{-1}$ to the area of the of the C—H absorption peak centered near 1370 $cm^{-1}$. The area of the trans-vinylene absorptions (—C═C—) centered near 965 $cm^{-1}$ is related to the amount of crosslinking experienced by the material when exposed to ionizing radiation. Polymer main chain unsaturation in the form of trans-vinyl groups are a side reaction during crosslinking via ionizing radiation such as gamma, x-ray and electron beam. The correlation between TVI and actual received radiation dose can depend on the nature of the irradiation conditions, for example, radiation source (gamma or electron beam), temperature, dose rate, and oxygen level. The amount of unsaturation formation can be directly correlated with the amount of irradiation (e.g., dose), and can be used as a dosimeter for a given material and irradiation method combination.

Top-to-bottom OI results for Sample 4-1 are shown in Table 1, where the interior 100 are the center 100 data collection points in the scan which are used to establish the zero baseline for OI determination. Side-to-side OI results for Sample 4-1 are shown in Table 2. Top-to-bottom TVI results for Sample 4-1 are shown in Table 3. Side-to-side TVI results for Sample 4-1 are shown in Table 4.

TABLE 1

| Oxidation Results: | OI | |
| --- | --- | --- |
| Avg & SD OI, All Data: | 0.0815 | 0.3345 |
| Avg & SD OI, Interior 100: | 0.0000 | 0.0030 |

TABLE 2

| Oxidation Results: | OI | |
| --- | --- | --- |
| Avg & SD OI, All Data: | 0.0402 | 0.2231 |
| Avg & SD OI, Interior 100: | 0.0000 | 0.0014 |

TABLE 3

Trans-Vinyl Results (ASTM):

| Avg & SD TVI, All Data: | 0.0371 | 0.0036 |
| --- | --- | --- |

TABLE 4

Trans-Vinyl Results (ASTM):

| Avg & SD TVI, All Data: | 0.0373 | 0.0026 |
| --- | --- | --- |

Figure 3A:
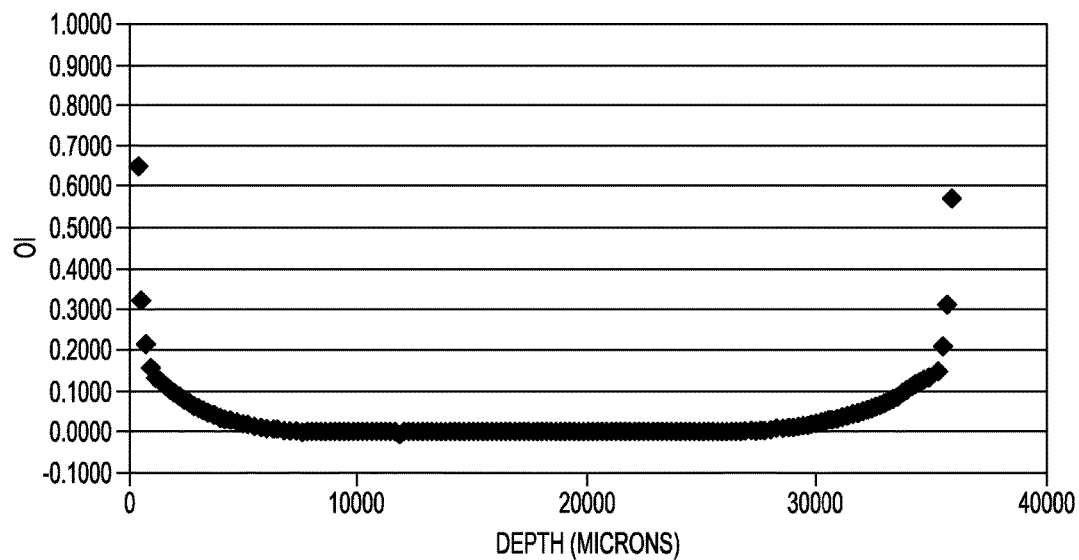
FIGS. 3A-B illustrate oxidative index (OI) for Sample 4-1, with FIG. 3A showing the top-to-bottom profile, and with FIG. 3B showing the side-to-side profile, in accordance with various embodiments.
Figure 3B:
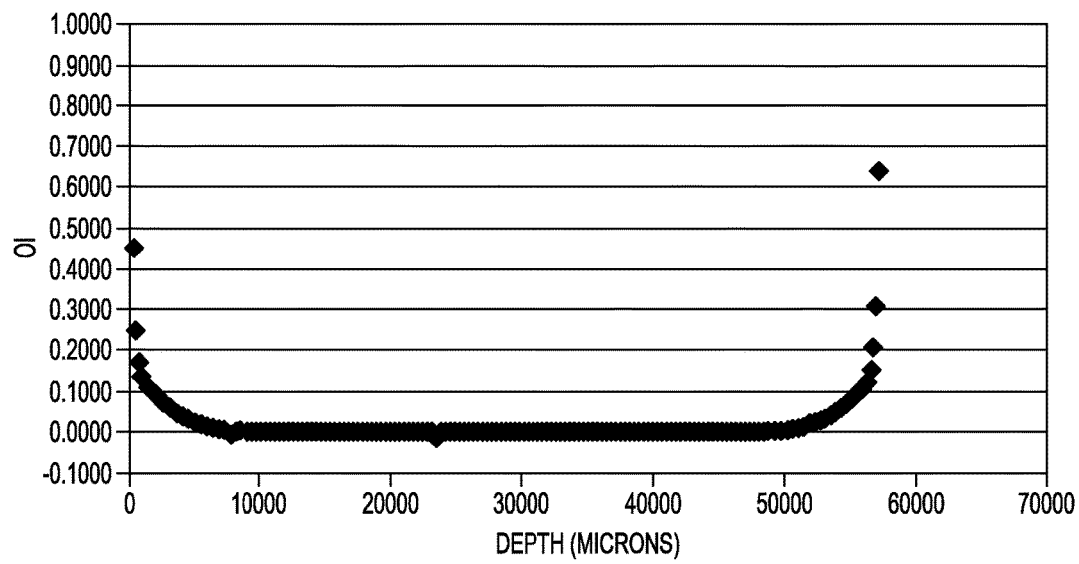
Figure 4A:
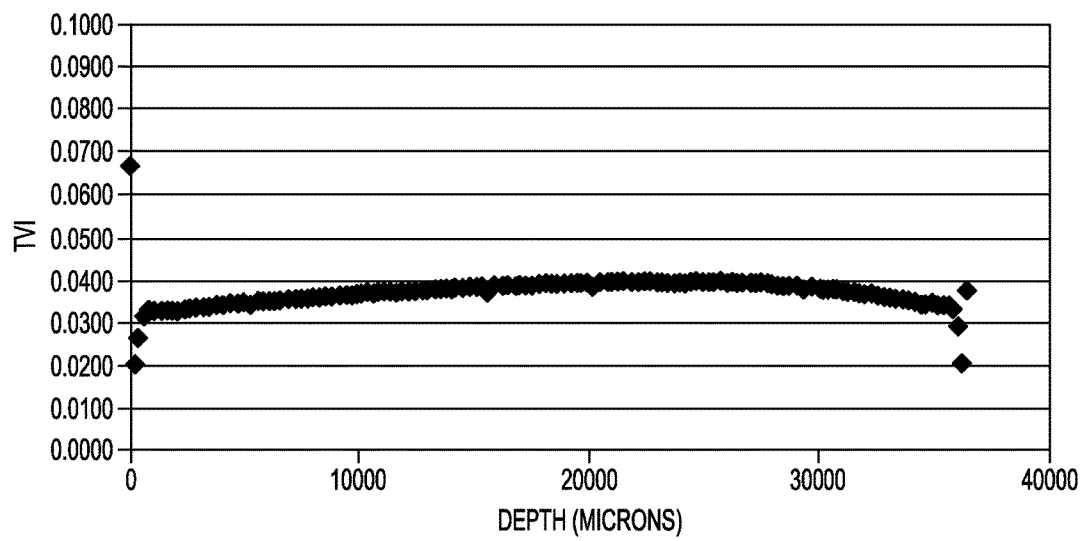
FIGS. 4A-B illustrate transvinylene index (TVI) for Sample 4-1, with FIG. 4A showing the top-to-bottom profile, and with FIG. 4B showing the side-to-side profile, in accordance with various embodiments.
Figure 4B:
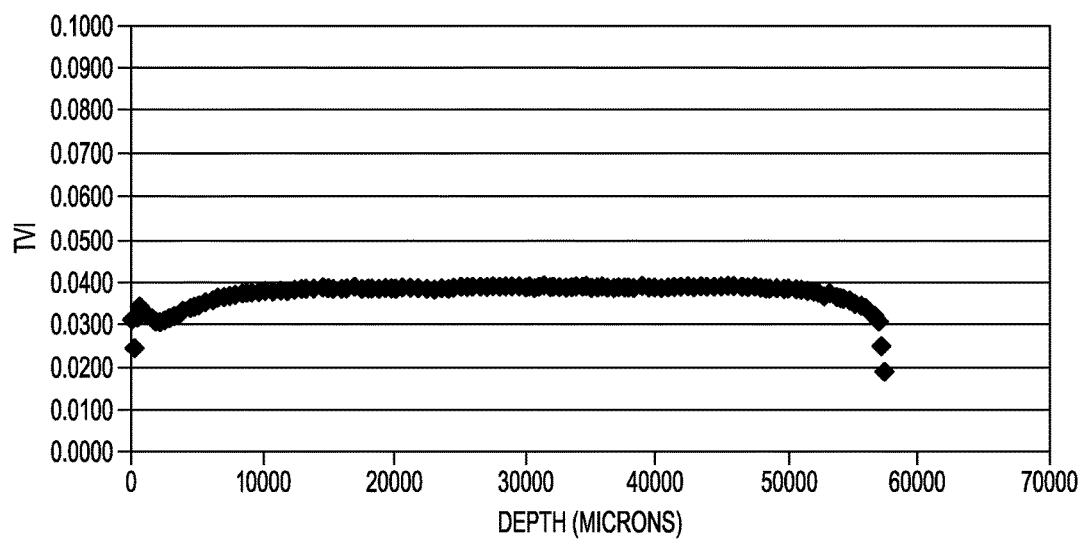

FIGS. 3A-B illustrate OI for Sample 4-1, with FIG. 3A showing the top-to-bottom profile, and with FIG. 3B showing the side-to-side profile. FIGS. 4A-B illustrate TVI results for Sample 4-1, with FIG. 4A showing the top-to-bottom profile, and with FIG. 4B showing the side-to-side profile.

Top-to-bottom OI results for Sample 4-2 are shown in Table 5. Side-to-side OI results for Sample 4-2 are shown in Table 6. Top-to-bottom TVI results for Sample 4-2 are shown in Table 7. Side-to-side TVI results for Sample 4-2 are shown in Table 8.

TABLE 5

| Oxidation Results: | OI | |
| --- | --- | --- |
| Avg & SD OI, All Data: | −0.0005 | 0.0026 |
| Avg & SD OI, Interior 100: | 0.0000 | 0.0014 |

TABLE 6

| Oxidation Results: | OI | |
| --- | --- | --- |
| Avg & SD OI, All Data: | −0.0001 | 0.0028 |
| Avg & SD OI, Interior 100: | 0.0000 | 0.0016 |

TABLE 7

Trans-Vinyl Results (ASTM):

| Avg & SD TVI, All Data: | 0.0381 | 0.0018 |
| --- | --- | --- |

TABLE 8

Trans-Vinyl Results (ASTM):

| Avg & SD TVI, All Data: | 0.0380 | 0.0020 |
| --- | --- | --- |

Figure 5A:
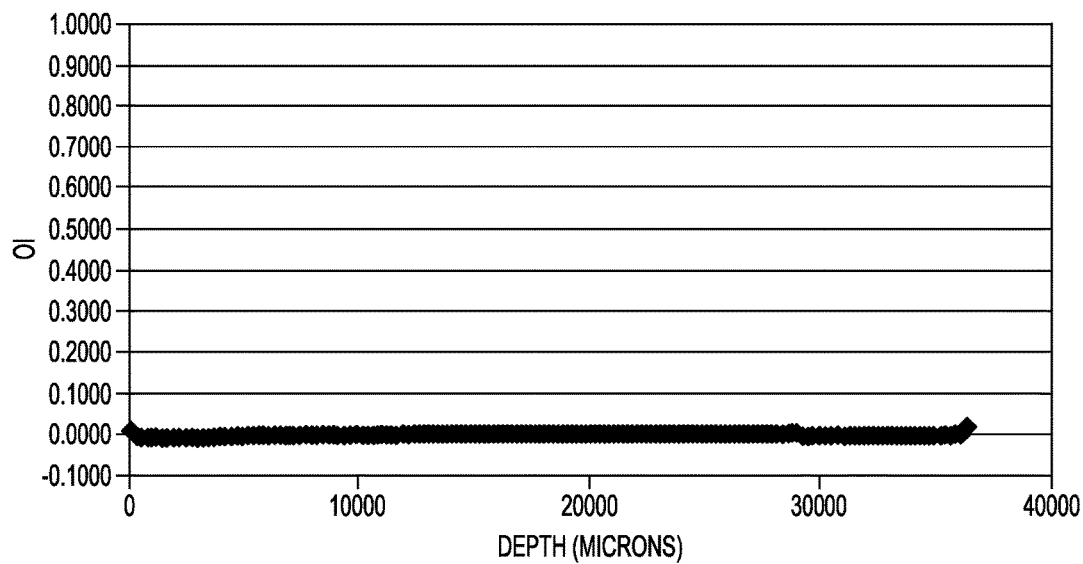
FIGS. 5A-B illustrate oxidative index (OI) for Sample 4-2, with FIG. 5A showing the top-to-bottom profile, and with FIG. 5B showing the side-to-side profile, in accordance with various embodiments.
Figure 5B:
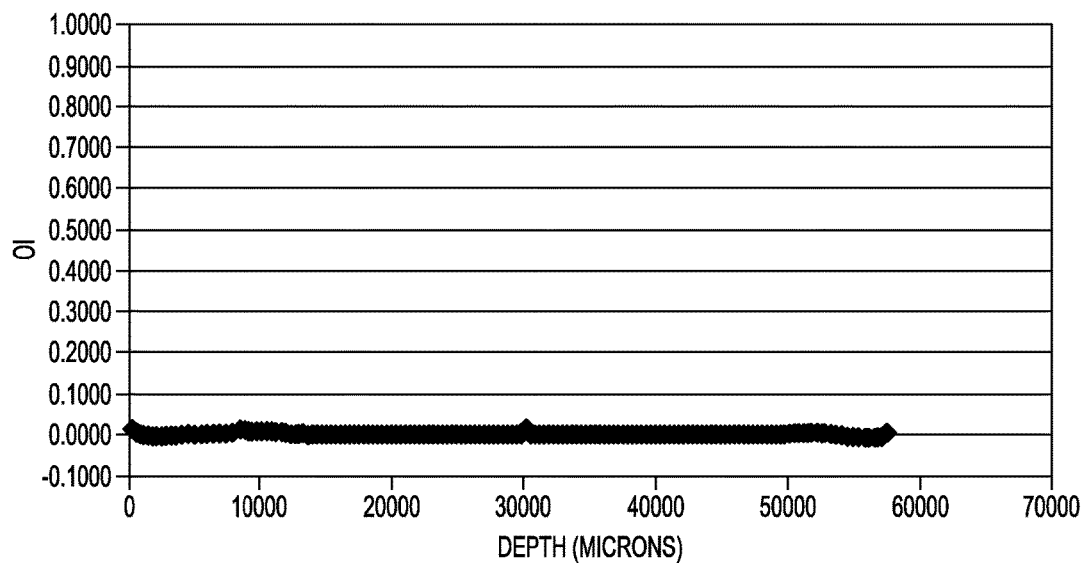
Figure 6A:
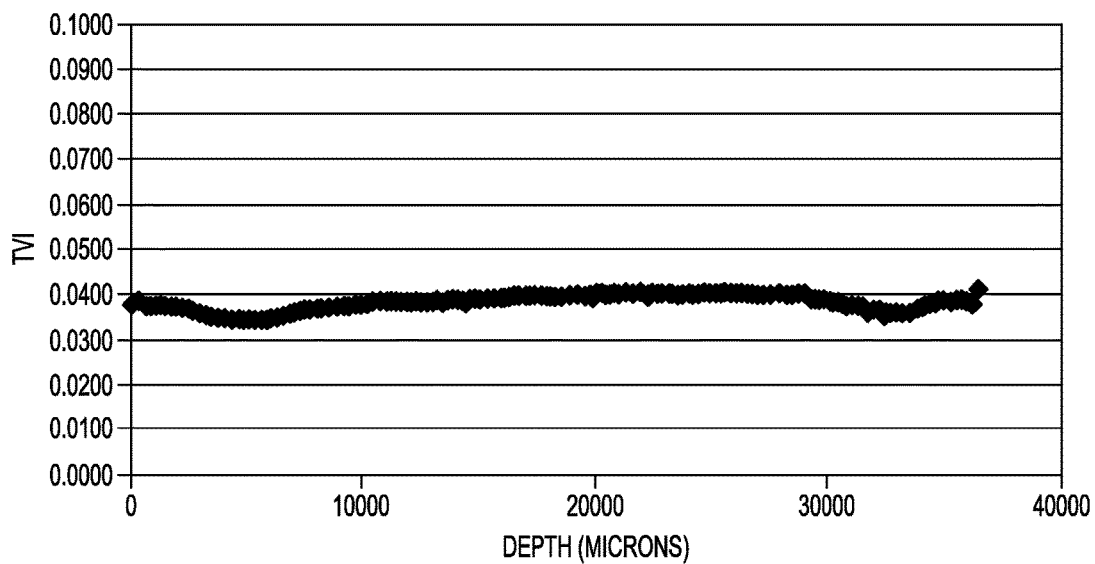
FIGS. 6A-B illustrate transvinylene index (TVI) for Sample 4-2, with FIG. 6A showing the top-to-bottom profile, and with FIG. 6B showing the side-to-side profile, in accordance with various embodiments.
Figure 6B:
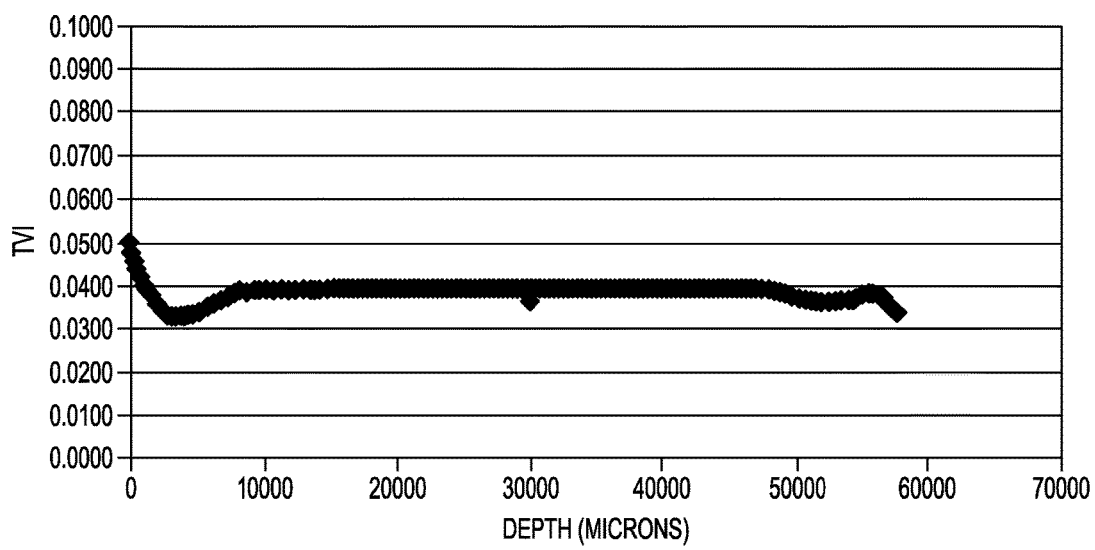

FIGS. 5A-B illustrate OI for Sample 4-2, with FIG. 5A showing the top-to-bottom profile, and with FIG. 5B showing the side-to-side profile. FIGS. 6A-B illustrate TVI results for Sample 4-2, with FIG. 6A showing the top-to-bottom profile, and with FIG. 6B showing the side-to-side profile.

Top-to-bottom OI results for Sample 4-3 are shown in Table 9. Side-to-side OI results for Sample 4-3 are shown in Table 10. Top-to-bottom TVI results for Sample 4-3 are shown in Table 11. Side-to-side TVI results for Sample 4-3 are shown in Table 12.

TABLE 9

| Oxidation Results: | OI | |
| --- | --- | --- |
| Avg & SD OI, All Data: | −0.0039 | 0.0758 |
| Avg & SD OI, Interior 100: | 0.0000 | 0.1009 |

TABLE 10

| Oxidation Results: | OI | |
| --- | --- | --- |
| Avg & SD OI, All Data: | 0.0017 | 0.0030 |
| Avg & SD OI, Interior 100: | 0.0000 | 0.0022 |

TABLE 11

| Trans-Vinyl Results (ASTM): | | |
| --- | --- | --- |
| Avg & SD TVI, All Data: | 0.0454 | 0.0124 |

TABLE 12

| Trans-Vinyl Results (ASTM): | | |
| --- | --- | --- |
| Avg & SD TVI, All Data: | 0.0439 | 0.0120 |

Figure 7A:
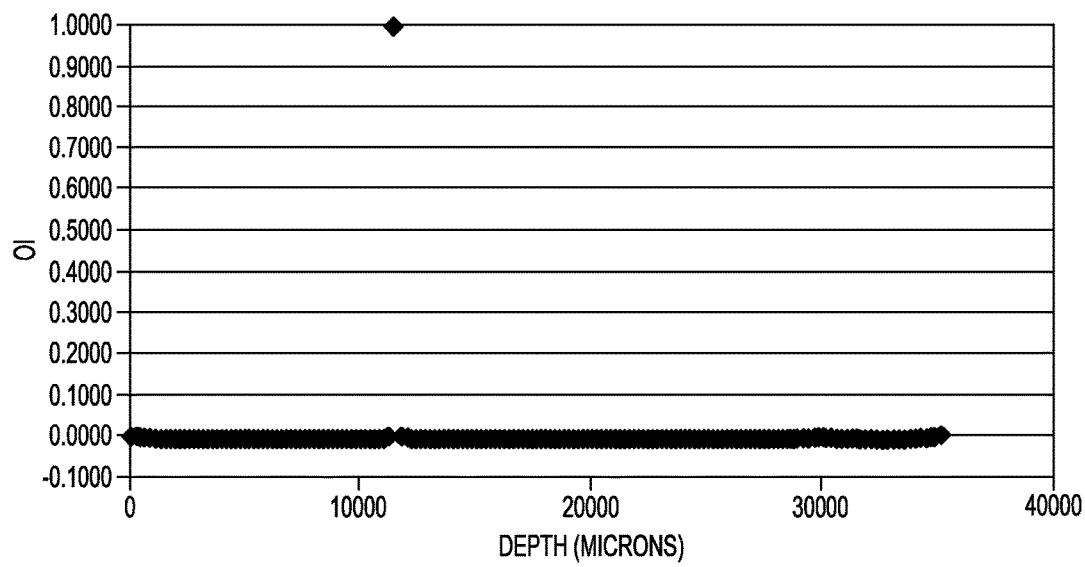
FIGS. 7A-B illustrate oxidative index (OI) for Sample 4-3, with FIG. 7A showing the top-to-bottom profile, and with FIG. 7B showing the side-to-side profile, in accordance with various embodiments.
Figure 7B:
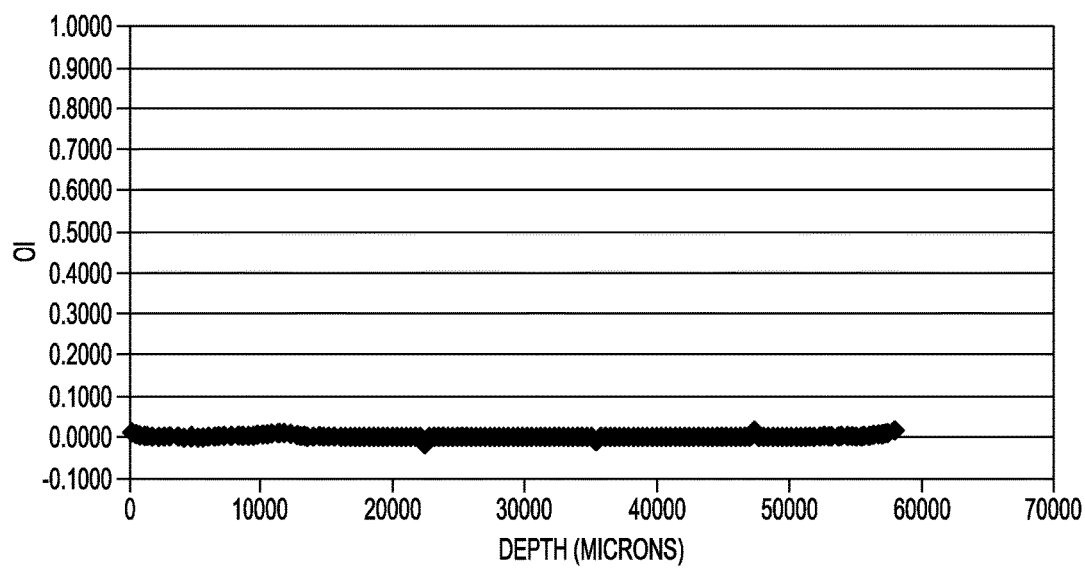
Figure 8A:
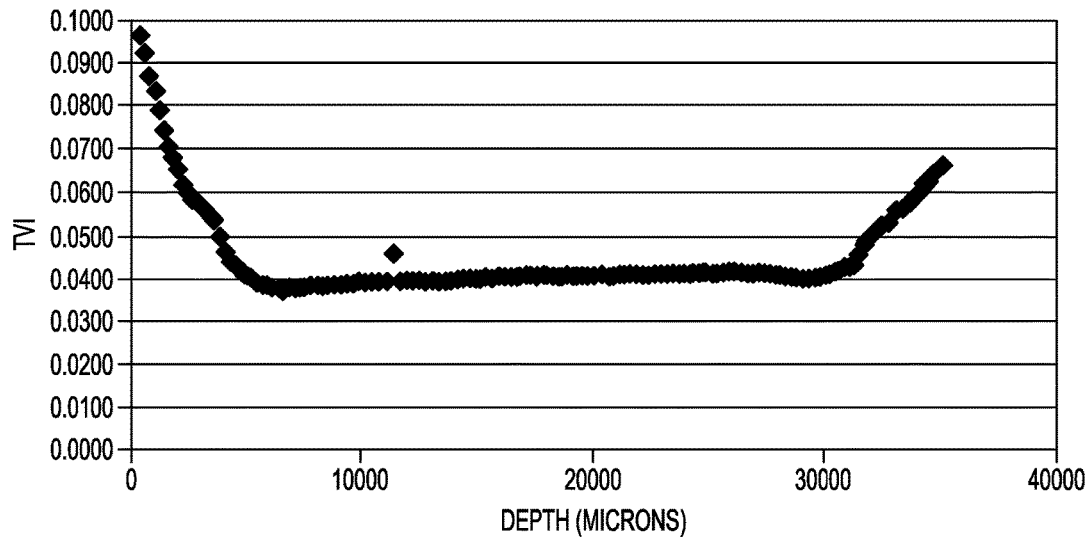
FIGS. 8A-B illustrate transvinylene index (TVI) for Sample 4-3, with FIG. 8A showing the top-to-bottom profile, and with FIG. 8B showing the side-to-side profile, in accordance with various embodiments.
Figure 8B:
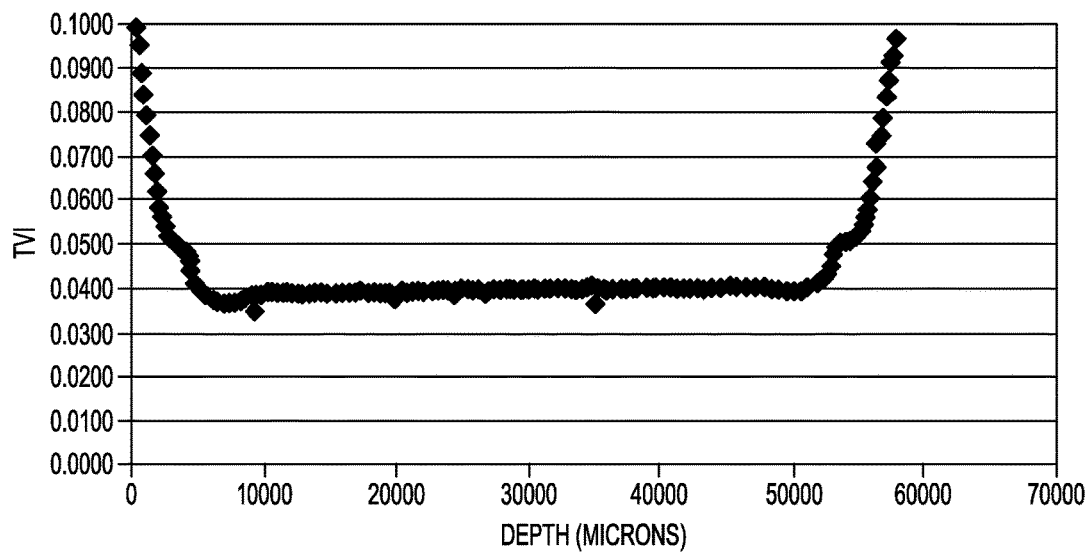

FIGS. 7A-B illustrate OI for Sample 4-3, with FIG. 7A showing the top-to-bottom profile, and with FIG. 7B showing the side-to-side profile. FIGS. 8A-B illustrate TVI results for Sample 4-3, with FIG. 8A showing the top-to-bottom profile, and with FIG. 8B showing the side-to-side profile.

Top-to-bottom OI results for Sample 4-4 are shown in Table 13. Side-to-side OI results for Sample 4-4 are shown in Table 14. Top-to-bottom TVI results for Sample 4-4 are shown in Table 15. Side-to-side TVI results for Sample 4-4 are shown in Table 16.

TABLE 13

| Oxidation Results: | OI | |
| --- | --- | --- |
| Avg & SD OI, All Data: | 0.0052 | 0.0131 |
| Avg & SD OI, Interior 100: | 0.0000 | 0.0015 |

TABLE 14

| Oxidation Results: | OI | |
| --- | --- | --- |
| Avg & SD OI, All Data: | 0.0035 | 0.0082 |
| Avg & SD OI, Interior 100: | 0.0000 | 0.0007 |

TABLE 15

| Trans-Vinyl Results (ASTM): | | |
| --- | --- | --- |
| Avg & SD TVI, All Data: | 0.0430 | 0.0116 |

TABLE 16

| Trans-Vinyl Results (ASTM): | | |
| --- | --- | --- |
| Avg & SD TVI, All Data: | 0.0422 | 0.0105 |

Figure 9A:
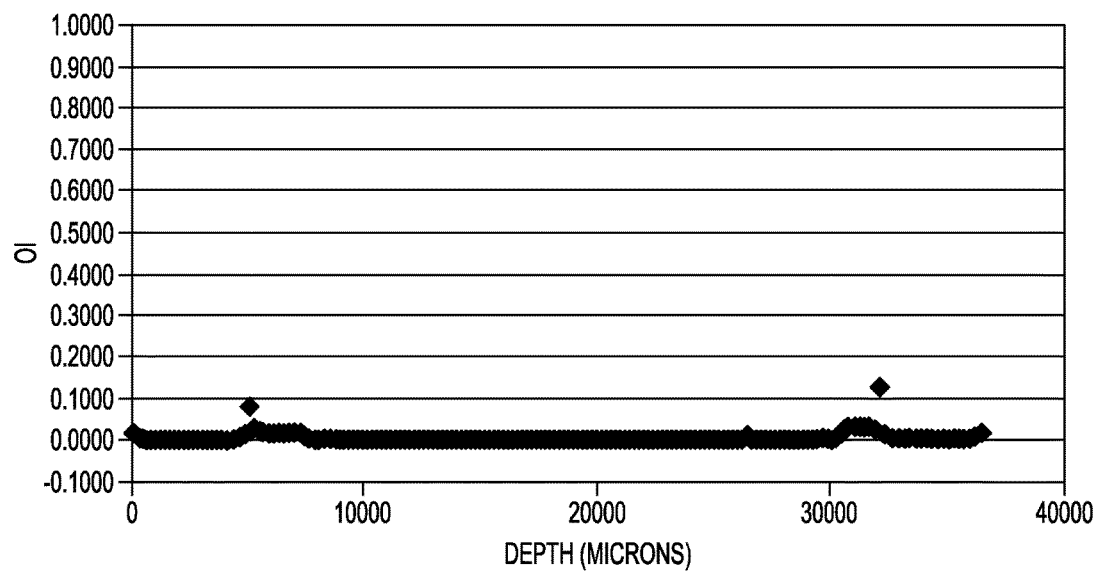
FIGS. 9A-B illustrate oxidative index (OI) for Sample 4-4, with FIG. 9A showing the top-to-bottom profile, and with FIG. 9B showing the side-to-side profile, in accordance with various embodiments.
Figure 9B:
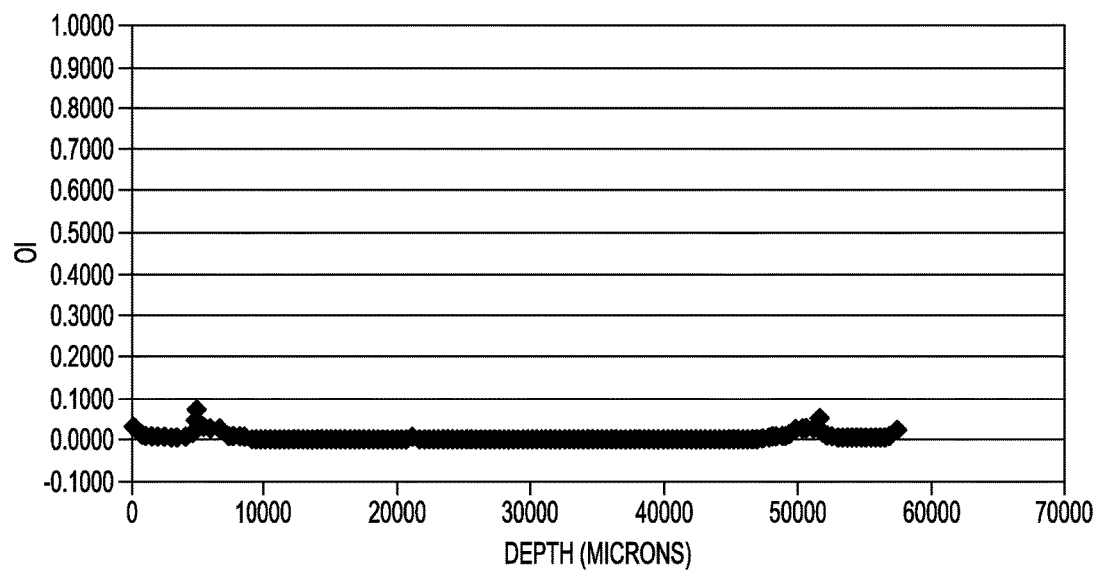
Figure 10A:
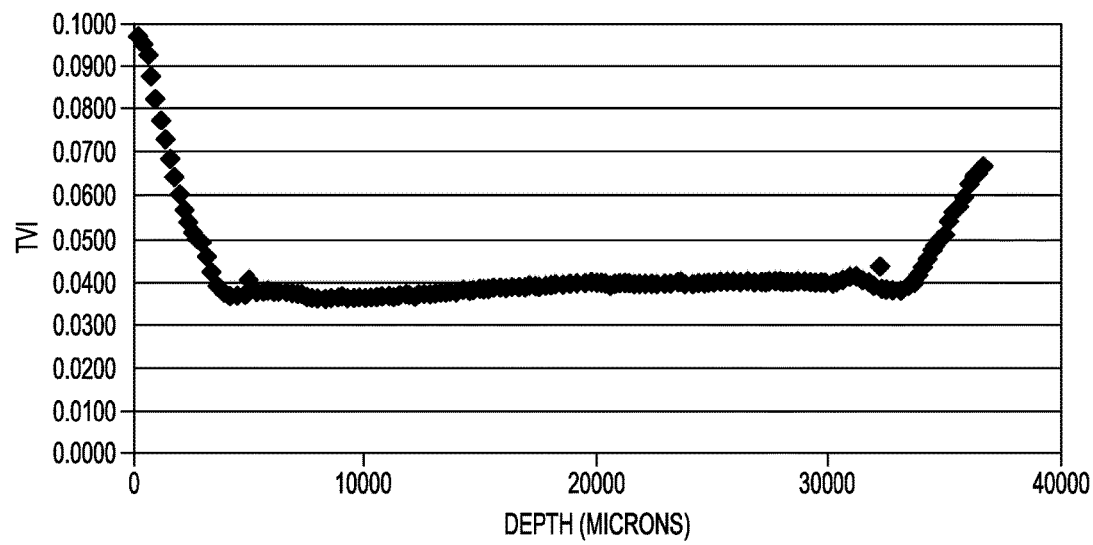
FIGS. 10A-B illustrate transvinylene index (TVI) for Sample 4-4, with FIG. 10A showing the top-to-bottom profile, and with FIG. 10B showing the side-to-side profile, in accordance with various embodiments.
Figure 10B:
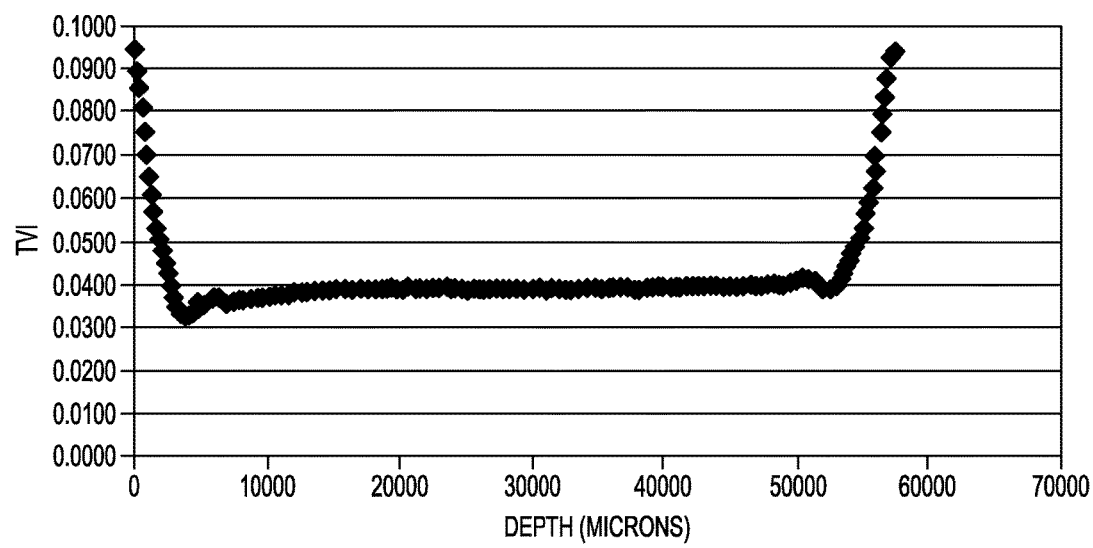

FIGS. 9A-B illustrate OI for Sample 4-4, with FIG. 9A showing the top-to-bottom profile, and with FIG. 9B showing the side-to-side profile. FIGS. 10A-B illustrate TVI results for Sample 4-4, with FIG. 10A showing the top-to-bottom profile, and with FIG. 10B showing the side-to-side profile.

Table 17 gives the depth in microns from outside surfaces (top, bottom, left side and right side) where oxidation index drops to below 0.1 or less for samples 4-1 through 4-4

TABLE 17

| Sample | Surface designation | Depth, microns, to ≤0.1 O.I. |
| --- | --- | --- |
| 4-1 | Top | 2200 |
| 4-1 | Bottom | 2600 |
| 4-1 | Left Side | 2000 |
| 4-1 | Right Side | 1800 |
| 4-2 | Top | 0 |
| 4-2 | Bottom | 0 |
| 4-2 | Left Side | 0 |
| 4-2 | Right Side | 0 |
| 4-3 | Top | 0 |
| 4-3 | Bottom | 0 |
| 4-3 | Left Side | 0 |
| 4-3 | Right Side | 0 |
| 4-4 | Top | 0 |
| 4-4 | Bottom | 0 |
| 4-4 | Left Side | 0 |
| 4-4 | Right Side | 0 |

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Additional Embodiments

The following exemplary embodiments are provided, the numbering of which is not to be construed as designating levels of importance:

Embodiment 1 provides a method of adding antioxidant to ultra high molecular weight polyethylene (UHMWPE), the method comprising:

obtaining or providing a porous solid material comprising UHMWPE;

coating the porous solid material with a liquid composition comprising at least one antioxidant such that at least some of the liquid composition enters void space of the porous solid material, to provide an antioxidant-infused solid material; and melt-consolidating the antioxidant-infused solid material, to provide a melt-consolidated material.

Embodiment 2 provides the method of Embodiment 1, wherein the porous solid material comprises about 0.001 vol % to about 80 vol % void space.

Embodiment 3 provides the method of any one of Embodiments 1-2, wherein the porous solid material comprises about 1 vol % to about 50 vol % void space.

Embodiment 4 provides the method of any one of Embodiments 1-3, wherein void space of the porous solid material is substantially homogenously distributed therein.

Embodiment 5 provides the method of any one of Embodiments 1-4, wherein about 1 wt % to about 100 wt % of the porous solid material is the UHMWPE.

Embodiment 6 provides the method of any one of Embodiments 1-5, wherein about 90 wt % to about 100 wt % of the porous solid material is the UHMWPE.

Embodiment 7 provides the method of any one of Embodiments 1-6, wherein the porous solid material is a cold-sintered UHMWPE powder.

Embodiment 8 provides the method of any one of Embodiments 1-7, further comprising cold-sintering UHMWPE powder, to provide the porous solid material.

Embodiment 9 provides the method of any one of Embodiments 1-8, wherein the porous solid material is free of melt-consolidation.

Embodiment 10 provides the method of any one of Embodiments 1-9, wherein the coating comprises at least one of selective coating and uniform coating.

Embodiment 11 provides the method of any one of Embodiments 1-10, wherein the coating the porous solid material comprises coating about 1% to about 100% of the porous solid material surface.

Embodiment 12 provides the method of any one of Embodiments 1-11, wherein the coating the porous solid material comprises coating about 90% to about 100% of the porous solid material surface.

Embodiment 13 provides the method of any one of Embodiments 1-12, wherein the coating comprises injecting the liquid composition into a mold comprising the porous solid material.

Embodiment 14 provides the method of Embodiment 13, further comprising injecting the liquid composition under a pressure into the mold comprising the porous solid material.

Embodiment 15 provides the method of any one of Embodiments 1-14, further comprising using a ram extruder to form the porous solid material comprising UHMWPE in a cold-sintering section of the ram extruder.

Embodiment 16 provides the method of Embodiment 15, further comprising using a melt-consolidating section of the ram extruder to perform the melt-consolidation of the antioxidant-infused solid material.

Embodiment 17 provides the method of any one of Embodiments 15-16, further comprising performing the coating of the porous solid material in the ram extruder after the cold-sintering section of the ram extruder.

Embodiment 18 provides the method of any one of Embodiments 1-17, wherein the coating is sufficient for the antioxidant to infuse into a surface layer of the porous solid material.

Embodiment 19 provides the method of Embodiment 18, wherein the surface layer comprises a layer of about 0 mm deep to about 1 mm deep.

Embodiment 20 provides the method of any one of Embodiments 18-19, wherein the surface layer comprises a layer of about 0.01 mm deep to about 20 mm deep.

Embodiment 21 provides the method of any one of Embodiments 18-20, wherein the coating is sufficient to provide a weight gain of about 0.000,01 g/cm$^2$ surface area to about 50 g/cm$^2$ surface area.

Embodiment 22 provides the method of any one of Embodiments 1-21, wherein the coating is sufficient to provide a weight gain of about 0.000,1 g/cm$^2$ surface area to about 1 g/cm$^2$ surface area.

Embodiment 23 provides the method of any one of Embodiments 1-22, comprising controlling a depth of penetration of the antioxidant into the porous solid material by at least one of a pressure of the coating, a duration of the coating, a quantity of the liquid composition used during the coating, a concentration of the antioxidant in the liquid composition used during the coating, a molecular weight of the antioxidant, and a polarity of the antioxidant.

Embodiment 24 provides the method of any one of Embodiments 1-23, wherein the liquid composition comprises a solvent, further comprising heating the antioxidant-infused solid material to remove at least some of the solvent from the antioxidant-infused solid material prior to or during the melt-consolidation.

Embodiment 25 provides the method of any one of Embodiments 1-24, wherein the liquid composition further comprises an organic peroxide.

Embodiment 26 provides the method of any one of Embodiments 1-25, comprising controlling a depth of penetration of the antioxidant into the porous solid material by controlling at least one of the temperature reached during the melt-consolidating and the duration of the melt-consolidating.

Embodiment 27 provides the method of any one of Embodiments 1-26, further comprising preheating the melt-consolidated material before an irradiation.

Embodiment 28 provides the method of any one of Embodiments 1-27, further comprising irradiating the melt-consolidated material.

Embodiment 29 provides the method of Embodiment 28, wherein the irradiating comprises an irradiation dose of about 1 kGy to about 100,000 kGy.

Embodiment 30 provides the method of any one of Embodiments 28-29, wherein the irradiating comprises an irradiation dose of about 50 kGy to about 500 kGy.

Embodiment 31 provides the method of any one of Embodiments 28-30, wherein the irradiating comprises an irradiation dose rate of about 0.001 mGy/h to about 500 MGy/h.

Embodiment 32 provides the method of any one of Embodiments 28-31, wherein the irradiating comprises an irradiation dose rate of about 1 mGy/h to about 50 MGy/h.

Embodiment 33 provides the method of any one of Embodiments 28-32, wherein the irradiating comprises at least one of electron beam irradiating and gamma irradiating.

Embodiment 34 provides the method of any one of Embodiments 1-33, further comprising
heating the melt-consolidated material sufficiently to melt at least part of the melt-consolidated material, to provide a heated material; and
solidifying the heated material, to provide a melt-stabilized material.

Embodiment 35 provides the method of Embodiment 34, wherein the melt-consolidated material that is heated is an irradiated melt-consolidated material.

Embodiment 36 provides the method of any one of Embodiments 34-35, wherein the melt-consolidated material is an irradiated, melt-consolidated material preheated prior to irradiation.

Embodiment 37 provides the method of any one of Embodiments 35-36, wherein the melt-consolidated material has a first concentration of free-radicals, and the melt-stabilized material has a second concentration of free-radicals, wherein the second concentration of free-radicals is less than the first concentration of free-radicals.

Embodiment 38 provides the method of Embodiment 37, wherein the first concentration of free-radicals is at least about $1\times10^{15}$ spins/g.

Embodiment 39 provides the method of any one of Embodiments 37-38, wherein the first concentration of free-radicals is about $1\times10^{15}$ spins/gram to about $1\times10^{20}$ spins/g.

Embodiment 40 provides the method of any one of Embodiments 37-39, wherein the second concentration of free-radicals is less than about $1\times10^{15}$ spins/g.

Embodiment 41 provides the method of any one of Embodiments 37-40, wherein the second concentration of free-radicals is about $1\times10^5$ spins/g to about $1\times10^{15}$ spins/g.

Embodiment 42 provides the method of any one of Embodiments 37-41, wherein the second concentration of free-radicals is about 1% to about 0.000,1% of the first concentration of free-radicals.

Embodiment 43 provides the method of any one of Embodiments 37-42, wherein the second concentration of free-radicals is about 0.1% to about 0.001% of the first concentration of free-radicals.

Embodiment 44 provides the method of any one of Embodiments 34-43, wherein the UHMWPE in a surface layer of the melt-stabilized material has an oxidation index that does not exceed 1.

Embodiment 45 provides the method of Embodiment 44, wherein the surface layer of the melt-stabilized material has an oxidation index of about 0.001 to about 1.

Embodiment 46 provides the method of any one of Embodiments 34-45, wherein the heating is performed in an environment comprising oxygen.

Embodiment 47 provides the method of Embodiment 46, wherein the environment comprising oxygen is about 1 vol % to about 50 vol % oxygen.

Embodiment 48 provides the method of any one of Embodiments 46-47, wherein the environment comprising oxygen is about 10 vol % to about 30 vol % oxygen.

Embodiment 49 provides the method of any one of Embodiments 34-48, wherein the heating that is sufficient to melt at least part of the melt-consolidated material comprises heating to about 100° C. to about 400° C.

Embodiment 50 provides the method of any one of Embodiments 34-49, wherein the heating that is sufficient to melt at least part of the melt-consolidated material comprises heating to about 140° C. to about 160° C.

Embodiment 51 provides the method of any one of Embodiments 34-50, wherein the heating that is sufficient to melt at least part of the melt-consolidated material comprises heating for about 1 minute to about 7 days.

Embodiment 52 provides the method of any one of Embodiments 34-51, wherein the heating that is sufficient to melt at least part of the melt-consolidated material comprises heating for about 1 hour to about 48 hours.

Embodiment 53 provides the method of any one of Embodiments 1-52, wherein the antioxidant is a free-radical scavenger.

Embodiment 54 provides the method of any one of Embodiments 1-53, wherein the antioxidant comprises at least one of a tocopherol, a tocopherol phosphite, a tocotrienol, vitamin E, vitamin E acetate, vitamin E phosphite, rosemary oil, pentaerythritol tetrakis(3-(3,5-di-tert-butyl-4-hydroxyphenyl)propionate), butanedioic acid dimethyl ester/4-hydroxy-2,2,6,6-tetramethyl-1-piperidine ethanol copolymer, tannic acid, bilberry extract, vitamin C, a carotene, a flavonoid, an isoflavonoid, a neoflavonoid, a lignin, quinine, ubiquinone, vitamin K1, a metal, glutathione, propyl gallate, octyl gallate, lauryl gallate, resveratrol, rosmarinic acid, rutin, 5-aminosalicylic acid, butylated hydroxy anisole, butylated hydroxy toluene, a phenolic compound, and a monomeric or polymeric hindered amine stabilizer.

Embodiment 55 provides the method of any one of Embodiments 1-54, wherein the antioxidant comprises at least one of vitamin E, vitamin E acetate, pentaerythritol tetrakis(3-(3,5-di-tert-butyl-4-hydroxyphenyl)propionate), butanedioic acid dimethyl ester/4-hydroxy-2,2,6,6-tetramethyl-1-piperidine ethanol copolymer, tannic acid, and bilberry extract.

Embodiment 56 provides the method of any one of Embodiments 1-55, wherein the antioxidant comprises at least one of racemic alpha-tocopherol, RRR-alpha-tocopherol, SRR-alpha-tocopherol, SSR-alpha-tocopherol, SRS-alpha-tocopherol, SSS-alpha-tocopherol, RSR-alpha-tocopherol, RRS-alpha-tocopherol, RSS-alpha-tocopherol, racemic beta-tocopherol, RRR-beta-tocopherol, SRR-beta-tocopherol, SSR-beta-tocopherol, SRS-beta-tocopherol, SSS-beta-tocopherol, RSR-beta-tocopherol, RRS-beta-tocopherol, RSS-beta-tocopherol, racemic gamma-tocopherol, RRR-gamma-tocopherol, SRR-gamma-tocopherol, SSR-gamma-tocopherol, SRS-gamma-tocopherol, SSS-gamma-tocopherol, RSR-gamma-tocopherol, RRS-gamma-tocopherol, RSS-gamma-tocopherol, racemic delta-tocopherol, RRR-delta-tocopherol, SRR-delta-tocopherol, SSR-delta-tocopherol, SRS-delta-tocopherol, SSS-delta-tocopherol, RSR-delta-tocopherol, RRS-delta-tocopherol, and RSS-delta-tocopherol.

Embodiment 57 provides the method of any one of Embodiments 1-56, wherein the antioxidant is about 0.01 wt % to about 100 wt % of the liquid composition.

Embodiment 58 provides the method of any one of Embodiments 1-57, wherein the antioxidant is about 1 wt % to about 100 wt % of the liquid composition.

Embodiment 59 provides the melt-stabilized material of any one of Embodiments 34-58.

Embodiment 60 provides an orthopedic implant comprising the melt-stabilized material of any one of Embodiments 34-58.

Embodiment 61 provides a method of preparing an orthopedic implant comprising forming an orthopedic implant from the melt-stabilized material of any one of Embodiments 34-58.

Embodiment 62 provides a method of adding antioxidant to ultra high molecular weight polyethylene (UHMWPE), the method comprising:

obtaining or providing a porous solid material comprising UHMWPE, wherein the porous solid material has a void space of about 0.001 vol % to about 80 vol %;

coating the porous solid material with a liquid composition comprising at least one antioxidant such that at least some of the liquid composition enters the void space of the porous solid material, to provide an antioxidant-infused solid material;

melt-consolidating the antioxidant-infused solid material, to provide a melt-consolidated material;

irradiating the melt-consolidated material using electron beam irradiation, to provide an irradiated material;

heating the irradiated material sufficiently to melt at least part of the irradiated material, to provide a heated material; and solidifying the heated material, to provide a melt-stabilized material.

Embodiment 63 provides a method of adding antioxidant to ultra high molecular weight polyethylene (UHMWPE), the method comprising:

cold-sintering a UHMWPE powder, to provide a porous solid material comprising UHMWPE, wherein the porous solid material has a void space of about 0.001 vol % to about 80 vol %;

coating about 90% to about 100% of the porous solid material surface with a liquid composition comprising at least one antioxidant such that at least some of the liquid composition enters the void space of the porous solid material, to provide an antioxidant-infused solid material, wherein the antioxidant is about 1 wt % to about 100 wt % of the liquid composition;

melt-consolidating the antioxidant-infused solid material, to provide a melt-consolidated material;

irradiating the melt-consolidated material using electron beam irradiation, to provide an irradiated material comprising UHMWPE having a first concentration of free radicals of at least about $1\times10^{15}$ spins/g;

heating the irradiated material sufficient to melt at least part of the irradiated material, to provide a heated material; and solidifying the heated material, to provide a melt-stabilized material comprising UHMWPE having a second concentration of free-radicals of less than about $1\times10^{15}$ spins/g;

wherein the UHMWPE in a surface layer of the melt-stabilized material has an oxidation index that does not exceed about 1.

Embodiment 64 provides a medical implant comprising: an oxygen-containing-environment-melt-stabilized material comprising UHMWPE and an antioxidant, the antioxidant introduced prior to a melt-consolidation step and after a cold-sintering step, the melt-stabilized material being free of post-melt-stabilization-oxidized surface layer removal greater than about 3 mm depth, wherein the UHMWPE in a surface layer of the melt-stabilized material has an oxidation index that does not exceed about 1.

Embodiment 65 provides the method or implant of any one or any combination of Embodiments 1-64 optionally configured such that all elements or options recited are available to use or select from.

What is claimed is:

1. A method of adding antioxidant to ultra high molecular weight polyethylene (UHMWPE), the method comprising:
   coating a porous solid material comprising UHMWPE with a liquid composition comprising at least one antioxidant such that at least some of the liquid composition enters void space of the porous solid material, to provide an antioxidant-infused solid material, wherein the antioxidant is 3.5 wt % to 20 wt % of the antioxidant-infused solid material, wherein the porous solid material comprising UHMWPE comprises a cold-sintered UHMWPE powder;
   melt-consolidating the antioxidant-infused solid material, to provide a melt-consolidated material;
   irradiating the melt-consolidated material, to provide an irradiated material;
   heating the irradiated material sufficiently to melt at least part of the irradiated material, to provide a heated material; and
   solidifying the heated material, to provide a melt-stabilized material.

2. The method of claim 1, further comprising cold-sintering UHMWPE powder, to provide the porous solid material.

3. The method of claim 1, wherein the coating comprises injecting the liquid composition into a mold comprising the porous solid material.

4. The method of claim 1, wherein the coating is sufficient for the antioxidant to infuse into a surface layer of the porous solid material.

5. The method of claim 1, wherein the liquid composition comprises a solvent, further comprising heating the antioxidant-infused solid material to remove at least some of the solvent from the antioxidant-infused solid material prior to or during the melt-consolidation.

6. The method of claim 1, further comprising preheating the melt-consolidated material before an irradiation.

7. The method of claim 1, wherein the cold sintering comprises a maximum temperature of 115° C., wherein the UHMWPE is substantially free of melting during the cold-sintering.

8. The method of claim 1, wherein the irradiating comprises at least one of electron beam irradiating and gamma irradiating.

9. The method of claim 1, wherein the melt-consolidated material is an irradiated, melt-consolidated material preheated prior to irradiation.

10. The method of claim 1, wherein the melt-consolidated material has a first concentration of free-radicals, and the melt-stabilized material has a second concentration of free-radicals, wherein the second concentration of free-radicals is less than the first concentration of free-radicals.

11. The method of claim 10, wherein the second concentration of free-radicals is less than about $1\times10^{15}$ spins/g.

12. The method of claim 1, wherein the UHMWPE in a surface layer of the melt-stabilized material has an oxidation index that does not exceed 1.

13. The method of claim 1, wherein the heating is performed in an environment comprising oxygen.

14. The method of claim 1, wherein the antioxidant comprises at least one of a tocopherol; a tocopherol phosphite; a tocotrienol, vitamin E, vitamin E acetate, vitamin E phosphite, rosemary oil, pentaerythritol tetrakis(3-(3,5-di-tert-butyl-4-hydroxyphenyl)propionate), butanedioic acid dimethyl ester/4-hydroxy-2,2,6,6-tetramethyl-1-piperidine ethanol copolymer, tannic acid, bilberry extract, vitamin C, a carotene, a flavonoid, an isoflavonoid, a neoflavonoid, a lignin, quinine, ubiquinone, vitamin K1, a metal, glutathione, propyl gallate, octyl gallate, lauryl gallate, resveratrol; rosmarinic acid, rutin, 5-aminosalicylic acid, butylated hydroxy anisole, butylated hydroxy toluene, a phenolic compound, and a monomeric or polymeric hindered amine stabilizer.

15. The method of claim 1, wherein the antioxidant is about 0.01 wt % to about 100 wt % of the liquid composition.

16. The method of claim 1, wherein the method is a method of preparing an orthopedic implant, the method further comprising forming an orthopedic implant from the melt-stabilized material.

17. A method of adding antioxidant to ultra high molecular weight polyethylene (UHMWPE), the method comprising:
   cold-sintering a UHMWPE powder, to provide a porous solid material comprising UHMWPE, wherein the porous solid material has a void space of about 0.001 vol % to about 80 vol %, wherein the cold sintering comprises a maximum temperature of 115° C., wherein the UHMWPE is substantially free of melting during the cold-sintering;
   coating about 90% to about 100% of the porous solid material surface with a liquid composition comprising at least one antioxidant such that at least some of the liquid composition enters the void space of the porous solid material, to provide an antioxidant-infused solid material, wherein the antioxidant is about 1 wt % to about 100 wt % of the liquid composition, wherein the antioxidant is 3.5 wt % to 20 wt % of the antioxidant-infused solid material;
   melt-consolidating the antioxidant-infused solid material, to provide a melt-consolidated material;
   irradiating the melt-consolidated material using electron beam irradiation, to provide an irradiated material comprising UHMWPE having a first concentration of free radicals of at least about $1 \times 10^{15}$ spins/g;

heating the irradiated material sufficient to melt at least part of the irradiated material, to provide a heated material; and solidifying the heated material, to provide a melt-stabilized material comprising UHMWPE having a second concentration of free-radicals of less than about $1 \times 10^{15}$ spins/g;

wherein the UHMWPE in a surface layer of the melt-stabilized material has an oxidation index that does not exceed about 1.

18. The method of claim 1, wherein the melt-stabilized material is an oxygen-containing-environment-melt-stabilized material comprising UHMWPE and an antioxidant, the antioxidant introduced prior to a melt-consolidation step and after a cold-sintering step, the melt-stabilized material being free of post-melt-stabilization-oxidized surface layer removal greater than about 3 mm depth, wherein the UHMWPE in a surface layer of the melt-stabilized material has an oxidation index that does not exceed about 1.

* * * * *